(12) United States Patent
Gannon et al.

(10) Patent No.: US 12,239,675 B2
(45) Date of Patent: Mar. 4, 2025

(54) COMPOSITIONS FOR GUT HEALTH

(71) Applicant: INTERNATIONAL N&H DENMARK APS, Kongens Lyngby (DK)

(72) Inventors: John Thomas Gannon, Hockessin, DE (US); Michael W. Bostick, Wilmington, DE (US); Amanda Chan, Wilmington, DE (US); Raymond E. Jackson, Newark, DE (US); Victoria Vallejo Kelly, Wilmington, DE (US); Alexander D. Kopatsis, Wilmington, DE (US); Claus Lang, Palo Alto, CA (US); Qiong Wang, Palo Alto, CA (US); Julia Yager, Wilmington, DE (US); Rick W. Ye, Wilmington, DE (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 0 days.

(21) Appl. No.: 17/770,042

(22) PCT Filed: Oct. 16, 2020

(86) PCT No.: PCT/US2020/055937
§ 371 (c)(1),
(2) Date: Apr. 18, 2022

(87) PCT Pub. No.: WO2021/080864
PCT Pub. Date: Apr. 29, 2021

(65) Prior Publication Data
US 2022/0395543 A1 Dec. 15, 2022

Related U.S. Application Data

(60) Provisional application No. 62/923,781, filed on Oct. 21, 2019.

(51) Int. Cl.
| | | |
|---|---|---|
| *A23K 20/189* | (2016.01) |
| *A23K 10/18* | (2016.01) |
| *A23K 50/75* | (2016.01) |
| *A61K 9/00* | (2006.01) |
| *A61K 35/741* | (2015.01) |
| *A61K 35/742* | (2015.01) |
| *A61K 35/747* | (2015.01) |
| *A61K 38/46* | (2006.01) |
| *A61K 38/47* | (2006.01) |
| *A61K 38/48* | (2006.01) |
| *A61P 31/04* | (2006.01) |

(52) U.S. Cl.
CPC ............ *A61K 35/747* (2013.01); *A23K 10/18* (2016.05); *A23K 20/189* (2016.05); *A23K 50/75* (2016.05); *A61K 9/0056* (2013.01); *A61K 35/741* (2013.01); *A61K 35/742* (2013.01); *A61K 38/465* (2013.01); *A61K 38/47* (2013.01); *A61K 38/48* (2013.01); *A61P 31/04* (2018.01); *A23V 2400/173* (2023.08); *A23V 2400/181* (2023.08)

(58) Field of Classification Search
None
See application file for complete search history.

(56) References Cited

U.S. PATENT DOCUMENTS

2016/0143962 A1  5/2016  Berry et al.
2018/0333443 A1* 11/2018  Embree .................. C12N 1/205

FOREIGN PATENT DOCUMENTS

| CA | 3069567 A1 | 1/2019 | |
| CN | 103429093 A | 12/2013 | |
| CN | 102480995 B | 6/2014 | |
| CN | 102892303 B | 3/2016 | |
| CN | 107249609 A | 10/2017 | |
| WO | WO-2017181203 A1 * | 10/2017 | ............. A01K 45/00 |

OTHER PUBLICATIONS

Han et al., "Evaluating the association between body weight and the intestinal microbiota of weaned piglets via 16S rRNA sequencing", Applied Microbiology and Biotechnology, vol. 101, pp. 5903-5911. (Year: 2017).*

* cited by examiner

Primary Examiner — Michelle F. Paguio Frising
Assistant Examiner — Grant C Currens

(57) ABSTRACT

Provided herein, inter alia, are compositions of short chain fatty acid (SCFA)-producing microorganisms and methods of making and using the same to inhibit pathogenic bacterial populations in the gastrointestinal tracts of an animal and additionally promote improvement of one or more metrics in an animal, such as increased bodyweight gain, decreased feed conversion ratio (FCR), improved gut barrier integrity, reduced mortality, reduced pathogen infection, and reduced pathogen shedding in feces.

6 Claims, 3 Drawing Sheets

Specification includes a Sequence Listing.

SEQUENCE LISTING

<160> NUMBER OF SEQ ID NOS: 22

<210> SEQ ID NO 1
<211> LENGTH: 1305
<212> TYPE: DNA
<213> ORGANISM: Anaerotruncus colihominis

<400> SEQUENCE: 1

| | | | | | |
|---|---|---|---|---|---|
| caaaggagca | atccgctgaa | agatgggctc | gcgtccgatt | agccagttgg | cggggtaacg | 60 |
| gcccaccaaa | gcgacgatcg | gtagccggac | tgagaggttg | aacggccaca | ttgggactga | 120 |
| gacacggccc | agactcctac | gggaggcagc | agtgggggat | attgcacaat | gggcgaaagc | 180 |
| ctgatgcagc | gacgccgcgt | gagggaagac | ggtcttcgga | ttgtaaacct | ctgtctttgg | 240 |
| ggaagaaaat | gacggtaccc | aaagaggaag | ctccggctaa | ctacgtgcca | gcagccgcgg | 300 |
| taatacgtag | ggagcaagcg | ttgtccggaa | ttactgggtg | taagggagc | gtaggcggga | 360 |
| tggcaagtag | aatgttaaat | ccatcggctc | aaccggtggc | tgcgttctaa | actgccgttc | 420 |
| ttgagtgaag | tagaggcagg | cggaattcct | agtgtagcgg | tgaaatgcgt | agatattagg | 480 |
| aggaacacca | gtggcgaagg | cggcctgctg | gctttaact | gacgctgagg | ctcgaaagcg | 540 |
| tggggagcaa | acaggattag | ataccctggt | agtccacgcc | gtaaacgatg | attactaggt | 600 |
| gtgggggac | tgacccttc | cgtgccgcag | ttaacacaat | aagtaatcca | cctggggagt | 660 |
| acggccgcaa | ggttgaaact | caaaggaatt | gacggggcc | cgcacaagca | gtggagtatg | 720 |
| tggtttaatt | cgaagcaacg | cgaagaacct | taccaggtct | tgacatcgga | tgcatagcct | 780 |
| ggagacaggt | gaagcccttc | ggggcatcca | gacaggtggt | gcatggttgt | cgtcagctcg | 840 |
| tgtcgtgaga | tgttgggtta | agtcccgcaa | cgagcgcaac | ccttattatt | agttgctacg | 900 |
| caagagcact | ctaatgagac | tgccgttgac | aaaacggagg | aaggtgggga | tgacgtcaaa | 960 |
| tcatcatgcc | ccttatgacc | tgggctacac | acgtactaca | atggcactta | aacagagggc | 1020 |
| ggcgacaccg | cgaggtgaag | cgaatcccga | aaaagtgtct | cagttcagat | gcaggctgc | 1080 |
| aacccgcctg | catgaagtcg | gaattgctag | taatcgcgga | tcagcatgcc | gcggtgaata | 1140 |
| cgttcccggg | ccttgtacac | accgcccgtc | acaccatggg | agtcggtaac | acccgaagcc | 1200 |
| agtagcctaa | ccgcaagggg | ggcgctgtcg | aaggtgggat | tgatgactgg | ggtgaagtcg | 1260 |
| taacaaggta | gccgtatcgg | aaggtgcggc | tggatcacct | ccttt | | 1305 |

<210> SEQ ID NO 2
<211> LENGTH: 1521
<212> TYPE: DNA
<213> ORGANISM: Anaerotruncus colihominis

<400> SEQUENCE: 2

| | | | | | |
|---|---|---|---|---|---|
| caaagagttt | gatcctggct | caggacgaac | gctggcggcg | cgcctaacac | atgcaagtcg | 60 |
| aacgggcctt | acattttgaa | gttttcggat | ggacgaatgt | aagcttagtg | gcggacgggt | 120 |
| gagtaacacg | tgagcaacct | gcctttcaga | gggggataac | agccgaaac | ggctgctaat | 180 |
| accgcataat | gttgcggggg | cacatgcccc | tgcaaccaaa | ggagcaatcc | gctgaaagat | 240 |

-continued

| | |
|---|---|
| gggctcgcgt ccgattagcc agttggcggg gtaacggccc accaaagcga cgatcggtag | 300 |
| ccggactgag aggttgaacg gccacattgg gactgagaca cggcccagac tcctacggga | 360 |
| ggcagcagtg ggggatattg cacaatgggc gaaagcctga tgcagcgacg ccgcgtgagg | 420 |
| gaagacggtc ttcggattgt aaacctctgt ctttggggaa gaaaatgacg gtacccaaag | 480 |
| aggaagctcc ggctaactac gtgccagcag ccgcggtaat acgtagggag caagcgttgt | 540 |
| ccggaattac tgggtgtaaa gggagcgtag gcgggatggc aagtagaatg ttaaatccat | 600 |
| cggctcaacc ggtggctgcg ttctaaactg ccgttcttga gtgaagtaga ggcaggcgga | 660 |
| attcctagtg tagcggtgaa atgcgtagat attaggagga acaccagtgg cgaaggcggc | 720 |
| ctgctgggct ttaactgacg ctgaggctcg aaagcgtggg gagcaaacag gattagatac | 780 |
| cctggtagtc cacgccgtaa acgatgatta ctaggtgtgg ggggactgac cccttccgtg | 840 |
| ccgcagttaa cacaataagt aatccacctg gggagtacgg ccgcaaggtt gaaactcaaa | 900 |
| ggaattgacg ggggcccgca caagcagtgg agtatgtggt ttaattcgaa gcaacgcgaa | 960 |
| gaaccttacc aggtcttgac atcggatgca tagcctggag acaggtgaag cccttcgggg | 1020 |
| catccagaca ggtggtgcat ggttgtcgtc agctcgtgtc gtgagatgtt gggttaagtc | 1080 |
| ccgcaacgag cgcaacccct tattattagtt gctacgcaag agcactctaa tgagactgcc | 1140 |
| gttgacaaaa cggaggaagg tggggatgac gtcaaatcat catgcccctt atgacctggg | 1200 |
| ctacacacgt actacaatgg cacttaaaca gagggcggcg acaccgcgag gtgaagcgaa | 1260 |
| tcccgaaaaa gtgtctcagt tcagattgca ggctgcaacc cgcctgcatg aagtcggaat | 1320 |
| tgctagtaat cgcggatcag catgccgcgg tgaatacgtt cccgggcctt gtacacaccg | 1380 |
| cccgtcacac catgggagtc ggtaacaccc gaagccagta gcctaaccgc aaggggggcg | 1440 |
| ctgtcgaagg tgggattgat gactggggtg aagtcgtaac aaggtagccg tatcggaagg | 1500 |
| tgcggctgga tcacctcctt t | 1521 |

<210> SEQ ID NO 3
<211> LENGTH: 1305
<212> TYPE: DNA
<213> ORGANISM: Anaerotruncus colihominis

<400> SEQUENCE: 3

| | |
|---|---|
| caaaggagca atccgctgaa agatgggctc gcgtccgatt agccagttgg cggggtaacg | 60 |
| gcccaccaaa gcgacgatcg gtagccggac tgagaggttg aacggccaca ttgggactga | 120 |
| gacacggccc agactcctac gggaggcagc agtgggggat attgcacaat gggcgaaagc | 180 |
| ctgatgcagc gacgccgcgt gagggaagac ggtcttcgga ttgtaaacct ctgtctttgg | 240 |
| ggaagaaaat gacggtaccc aaagaggaag ctccggctaa ctacgtgcca gcagccgcgg | 300 |
| taatacgtag ggagcaagcg ttgtccggaa ttactgggtg taaagggagc gtaggcggga | 360 |
| tggcaagtag aatgttaaat ccatcggctc aaccggtggc tgcgttctaa actgccgttc | 420 |
| ttgagtgaag tagaggcagg cggaattcct agtgtagcgg tgaaatgcgt agatattagg | 480 |
| aggaacacca gtggcgaagg cggcctgctg ggctttaact gacgctgagg ctcgaaagcg | 540 |
| tggggagcaa acaggattag ataccctggt agtccacgcc gtaaacgatg attactaggt | 600 |
| gtgggggac tgacccctc cgtgccgcag ttaacacaat aagtaatcca cctggggagt | 660 |
| acggccgcaa ggttgaaact caaaggaatt gacgggggcc cgcacaagca gtggagtatg | 720 |
| tggtttaatt cgaagcaacg cgaagaacct taccaggtct tgacatcgga tgcatagcct | 780 |
| ggagacaggt gaagcccttc ggggcatcca gacaggtggt gcatggttgt cgtcagctcg | 840 |

```
tgtcgtgaga tgttgggtta agtcccgcaa cgagcgcaac ccttattatt agttgctacg    900
caagagcact ctaatgagac tgccgttgac aaaacggagg aaggtgggga tgacgtcaaa    960
tcatcatgcc ccttatgacc tgggctacac acgtactaca atggcactta aacagagggc    1020
ggcgacaccg cgaggtgaag cgaatcccga aaaagtgtct cagttcagat tgcaggctgc    1080
aacccgcctg catgaagtcg gaattgctag taatcgcgga tcagcatgcc gcggtgaata    1140
cgttcccggg ccttgtacac accgcccgtc acaccatggg agtcggtaac acccgaagcc    1200
agtagcctaa ccgcaagggg ggcgctgtcg aaggtgggat tgatgactgg ggtgaagtcg    1260
taacaaggta gccgtatcgg aaggtgcggc tggatcacct ccttt    1305

<210> SEQ ID NO 4
<211> LENGTH: 1521
<212> TYPE: DNA
<213> ORGANISM: Anaerotruncus colihominis

<400> SEQUENCE: 4
caaagagttt gatcctggct caggacgaac gctggcggcg cgcctaacac atgcaagtcg    60 aacgggctt acattttgaa gttttcggat ggacgaatgt aagcttagtg gcggacgggt    120
gagtaacacg tgagcaacct gcctttcaga gggggataac agccggaaac ggctgctaat    180
accgcataat gttgcggggg cacatgcccc tgcaaccaaa ggagcaatcc gctgaaagat    240
gggctcgcgt ccgattagcc agttggcggg gtaacggccc accaaagcga cgatcggtag    300
ccggactgag aggttgaacg gccacattgg gactgagaca cggcccagac tcctacggga    360
ggcagcagtg ggggatattg cacaatgggc gaaagcctga tgcagcgacg ccgcgtgagg    420
gaagacggtc ttcggattgt aaacctctgt ctttggggaa gaaatgacg gtacccaaag    480 aggaagctcc ggctaactac gtgccagcag ccgcggtaat acgtagggag caagcgttgt    540
ccggaattac tgggtgtaaa gggagcgtag gcgggatggc aagtagaatg ttaaatccat    600
cggctcaacc ggtggctgcg ttctaaactg ccgttcttga gtgaagtaga ggcaggcgga    660
attcctagtg tagcggtgaa atgcgtagat attaggagga acaccagtgg cgaaggcggc    720
ctgctgggct ttaactgacg ctgaggctcg aaagcgtggg gagcaaacag gattagatac    780
cctggtagtc cacgccgtaa acgatgatta ctaggtgtgg ggggactgac cccttccgtg    840
ccgcagttaa cacaataagt aatccacctg ggagtacgg ccgcaaggtt gaaactcaaa    900
ggaattgacg ggggcccgca caagcagtgg agtatgtggt ttaattcgaa gcaacgcgaa    960
gaaccttacc aggtcttgac atcggatgca tagcctggag acaggtgaag cccttcgggg    1020
catccagaca ggtggtgcat ggttgtcgtc agctcgtgtc gtgagatgtt gggttaagtc    1080
ccgcaacgag cgcaaccctt attattagtt gctacgcaag agcactctaa tgagactgcc    1140
gttgacaaaa cggaggaagg tggggatgac gtcaaatcat catgcccctt atgacctggg    1200
ctacacacgt actacaatgg cactaaaaca gagggcggcg acaccgcgag gtgaagcgaa    1260
tcccgaaaaa gtgtctcagt tcagattgca ggctgcaacc cgcctgcatg aagtcggaat    1320
tgctagtaat cgcggatcag catgccgcgg tgaatacgtt cccgggcctt gtacacaccg    1380
cccgtcacac catgggagtc ggtaacaccc gaagccagta gcctaccgc aagggggcg    1440 ctgtcgaagg tgggattgat gactggggtg aagtcgtaac aaggtagccg tatcggaagg    1500
tgcggctgga tcacctcctt t    1521

<210> SEQ ID NO 5
```

```
<211> LENGTH: 1529
<212> TYPE: DNA
<213> ORGANISM: Coprococcus sp.

<400> SEQUENCE: 5
aacgagagtt tgatcctggc tcaggatgaa cgctggcggc gtgcctaaca catgcaagtc      60
gaacgaagca cttacttcca aatcttcgga agaggaggta cttgactgag tggcggacgg     120
gtgagtaacg cgtggggaac ctgccccgta ccggggata acagtcagaa atgactgcta     180
ataccgcata agcgcacgaa ggcgcatgct tttgtgtgaa aaactccggt ggtacgggat     240
ggtcccgcgt ctgattagcc agttggcggg gtaacggccc accaaagcga cgatcagtag     300
ccggcctgag agggtggacg gccacattgg gactgagaca cggcccagac tcctacggga     360
ggcagcagtg gggaatattg cacaatgggg gaaaccctga tgcagcgacg ccgcgtgagc     420
gaagaagtat ttcggtatgt aaagctctgt cagcagggaa gaaaatgacg gtacctgacc     480
aagaagcacc ggctaaatac gtgccagcag ccgcggtaat acgtatggtg caagcgttat     540
ccggatttac tgggtgtaaa gggagcgtag acggagggc aagtctgaag tgaaagcccg     600
gggcccaacc ccgggactgc tttggaaact gtccgtctgg agtgccggag aggtaagcgg     660
aattcccagt gtagcggtga aatgcgtaga tattgggagg aacaccagtg gcgaaggcgg     720
cttactggac ggtcactgac gttgaggctc gaaagcgtgg ggagcaaaca ggattagata     780
ccctggtagt ccacgccgta acgatgact actaggtgtc gggtggcaga gccattcggt     840
gccgcagcca acgcagtaag tagtccacct ggggagtacg ttcgcaagaa tgaaactcaa     900
aggaattgac ggggacccgc acaagcggtg gagcatgtgg tttaattcga agcaacgcga     960
agaaccttac ctggccttga catcccctg accgcgcgt aatggtgcct tccttcggg     1020 acaggggaga caggtggtgc atggttgtcg tcagctcgtg tcgtgagatg ttgggttaag    1080
tcccgcaacg agcgcaaccc ttatcttcag tagccagcac gcagaggtgg gcactctgga    1140
gagactgcca gggacaacct ggaggaaggt ggggatgacg tcaaatcatc atgcccctta    1200
tggccagggc tacacacgtg ctacaatggc gtaaacagag ggaagcgagc ccgcgagggg    1260
gagcaaatcc caaaaataac gtcccagttc ggactgcagg ctgcaacccg cctgcacgaa    1320
gctggaatcg ctagtaatcg cgaatcagca tgtcgcggtg aatacgttcc cgggtcttgt    1380
acacaccgcc cgtcacacca tgggagtcgg taacgcccga agtcagtgac caacctccg     1440 ggagggagct gccgaaggcg ggaccggtaa ctggggtgaa gtcgtaacaa ggtagccgta    1500
tcggaaggtg cggctggatc acctcctttt                                    1529

<210> SEQ ID NO 6
<211> LENGTH: 1521
<212> TYPE: DNA
<213> ORGANISM: Anaerotruncus colihominis

<400> SEQUENCE: 6
caaagagttt gatcctggct caggacgaac gctggcggcg cgcctaacac atgcaagtcg      60
aacggggctt acattttgaa gttttcggat ggacgaatgt aagcttagtg gcggacgggt     120
gagtaacacg tgagcaacct gcctttcaga ggggataac agccggaaac ggctgctaat     180
accgcataat gttgcggggg cacatgcccc tgcaaccaaa ggagcaatcc gctgaaagat     240
gggctcgcgt ccgattagcc agttggcggg gtaacggccc accaaagcga cgatcggtag     300
ccggactgag aggttgaacg gccacattgg gactgagaca cggcccagac tcctacggga     360
ggcagcagtg ggggatattg cacaatgggc gaaagcctga tgcagcgacg ccgcgtgagg     420
```

```
gaagacggtc ttcggattgt aaacctctgt ctttggggaa gaaaatgacg gtacccaaag      480
aggaagctcc ggctaactac gtgccagcag ccgcggtaat acgtagggag caagcgttgt      540
ccggaattac tgggtgtaaa gggagcgtag gcgggatggc aagtagaatg ttaaatccat      600
cggctcaacc ggtggctgcg ttctaaactg ccgttcttga gtgaagtaga ggcaggcgga      660
attcctagtg tagcggtgaa atgcgtagat attaggagga acaccagtgg cgaaggcggc      720
ctgctgggct ttaactgacg ctgaggctcg aaagcgtggg gagcaaacag gattagatac      780
cctggtagtc cacgccgtaa acgatgatta ctaggtgtgg ggggactgac cccttccgtg      840
ccgcagttaa cacaataagt aatccacctg gggagtacgg ccgcaaggtt gaaactcaaa      900
ggaattgacg ggggcccgca caagcagtgg agtatgtggt ttaattcgaa gcaacgcgaa      960
gaaccttacc aggtcttgac atcggatgca tagcctggag acaggtgaag cccttcgggg     1020
catccagaca ggtggtgcat ggttgtcgtc agctcgtgtc gtgagatgtt gggttaagtc     1080
ccgcaacgag cgcaacccct tattattagt gctacgcaag agcactctaa tgagactgcc     1140
gttgacaaaa cggaggaagg tggggatgac gtcaaatcat catgcccctt atgacctggg     1200
ctacacacgt actacaatgg cactaaaaca gagggcggcg acaccgcgag gtgaagcgaa     1260
tcccgaaaaa gtgtctcagt tcagattgca ggctgcaacc cgcctgcatg aagtcggaat     1320
tgctagtaat cgcggatcag catgccgcgg tgaatacgtt cccgggcctt gtacacaccg     1380
cccgtcacac catgggagtc ggtaacaccc gaagccagta gcctaaccgc aagggggggcg    1440 ctgtcgaagg tgggattgat gactggggtg aagtcgtaac aaggtagccg tatcggaagg     1500
tgcggctgga tcacctcctt t                                              1521
```

<210> SEQ ID NO 7
<211> LENGTH: 1425
<212> TYPE: DNA
<213> ORGANISM: Clostridium lactatifermentans

<400> SEQUENCE: 7

```
cttagtggcg gacgggtgag taacgtgtgg gcaacctgcc ctgtactggg gaataatcat       60
tggaaacgat gactaatacc gcatgtggtc ctcggaaggc atcttctgag gaagaaagga      120
tttattcggt acaggatggg cccgcatctg attagctagt tggtgagata acagcccacc      180
aaggcgacga tcagtagccg aactgagagg gtgatcggcc acattgggac tgagacacgg      240
cccaaactcc tacgggaggc agcagtgggg aatattgcac aatgggcgaa agcctgatgc      300
agcaacgccg cgtgaaggat gaagggtttc ggctcgtaaa cttctatcaa tagggaagaa      360
agaaatgacg gtacctaaat aagaagcccc ggctaactac gtgccagcag ccgcggtaat      420
acgtaggggg caagcgttat ccggaattac tgggtgtaaa gggagcgtag gcggcatggt      480
aagccagatg tgaaagcctt gggcttaacc cgaggattgc atttggaact atcaagctag      540
agtacaggag aggaaagcgg aattcctagt gtagcggtga atgcgtaga tattaggaag      600 aacaccagtg gcgaaggcgg ctttctggac tgaaactgac gctgaggctc gaaagcgtgg      660
ggagcaaaca ggattagata ccctggtagt ccacgccgta acgatgagt gctaggtgtc      720 ggggaggaat cctcggtgcc gcagctaacg caataagcac tccacctggg gagtacgacc      780
gcaaggttga aactcaaagg aattgacggg ggcccgcaca agcggtggag catgtggttt      840
aattcgaagc aacgcgaaga accttaccaa ggcttgacat cccgatgacc gctctagaga      900
tagagcttct cttcggagca tcggtgacag gtggtgcatg gttgtcgtca gctcgtgtcg      960
```

```
tgagatgttg ggttaagtcc cgcaacgagc gcaaccctta tcttcagtag ccatcattta      1020
gttgggcact ctggagagac tgccgtggat aacacggagg aaggtgggga tgacgtcaaa      1080
tcatcatgcc ccttatgtct tgggctacac acgtgctaca atggctggta acaaagtgac      1140
gcaaaacggc gacgttaagc aaatcacaaa aacccagtcc cagttcggat tgtagtctgc      1200
aactcgacta catgaagctg gaatcgctag taatcgcgaa tcagcatgtc gcggtgaata      1260
cgttcccggg ccttgtacac accgcccgtc acaccatggg agttggaagc acccgaagtc      1320
ggtgacctaa ccgtaaggaa ggagccgccg aaggtgaagc cagtgactgg ggtgaagtcg      1380
taacaaggta gccgtatcgg aaggtgcggc tggatcacct ccttt                     1425

<210> SEQ ID NO 8
<211> LENGTH: 1529
<212> TYPE: DNA
<213> ORGANISM: Pseudoflavonifractor capillosus

<400> SEQUENCE: 8
tattgagagt ttgatcctgg ctcaggatga acgctggcgg cgtgcttaac acatgcaagt        60
cgaacggaga gctaatgaca gaggattcgt ccaatggatt tagtttctta gtggcggacg       120
ggtgagtaac gcgtgaggaa cctgcctcgg agtggggaat aacacaacga agctgtgct        180 aataccgcat gatgcagctg gtcgcatga ctctggctgc aaagattta tcgctctgag        240 atggcctcgc gtctgattag ctggttggcg gggtaacggc ccaccaaggc gacgatcagt       300
agccggactg agaggttggc cggccacatt gggactgaga cacggcccag actcctacgg       360
gaggcagcag tggggaatat tgggcaatgg gcgcaagcct gacccagcaa cgccgcgtga       420
aggaagaagg ccctcgggtt gtaaacttct tttgtcaggg acgaagcaag tgacggtacc       480
tgacgaataa gccacggcta actacgtgcc agcagccgcg gtaatacgta ggtggcaagc       540
gttatccgga tttactgggt gtaaagggcg tgtaggcggg attgcaagtc agatgtgaaa       600
accacgggct caacctgtgg cctgcatttg aaactgcagt tcttgagtac tggagaggca       660
gacggaattc ctagtgtagc ggtgaaatgc gtagatatta ggaggaacac cagtggcgaa       720
ggcggtctgc tggacagcaa ctgacgctga ggcgcgaaag cgtggggagc aaacaggatt       780
agataccctg gtagtccacg ctgtaaacga tggatactag gtgtgggggg tctgacccct       840
tccgtgccgc agttaacaca ataagtatcc cacctgggga gtacgatcgc aaggttgaaa       900
ctcaaaggaa ttgacggggg cccgcacaag cggtggagta tgtggtttaa ttcgaagcaa       960
cgcgaagaac cttaccaggg cttgacatcc cgatgaccgg actagagata gtcttttctc      1020
ttcggagaca tcggtgacag gtggtgcatg gttgtcgtca gctcgtgtcg tgagatgttg      1080
ggttaagtcc cgcaacgagc gcaaccccta ttgttagttg ctacgcaaga gcactctagc      1140
gagactgccg ttgacaaaac ggaggaaggc ggggacgacg tcaaatcatc atgcccctta      1200
tgtcctgggc cacacacgta ctacaatggt ggttaacaga gggaggcaat accgcgaggt      1260
ggagcaaacc cctaaaagcc atcccagttc ggattgcagg ctgcaacccg cctgcatgaa      1320
gttggaatcg ctagtaatcg cggatcagca tgccgcggtg aatacgttcc cgggccttgt      1380
acacaccgcc cgtcacacca tgagagtcgg aacacccga agtccgtagc ctaaccgcaa       1440
ggggggcgcg gccgaaggtg ggttcgataa ttggggtgaa gtcgtaacaa ggtagccgta      1500
tcggaaggtg cggctggatc acctccttt                                       1529

<210> SEQ ID NO 9
<211> LENGTH: 1425
```

```
<212> TYPE: DNA
<213> ORGANISM: Clostridium lactatifermentans

<400> SEQUENCE: 9
cttagtggcg acgggtgag taacgtgtgg gcaacctgcc ctgtactggg gaataatcat      60
tggaaacgat gactaatacc gcatgtggtc ctcggaaggc atcttctgag gaagaaagga     120
tttattcggt acaggatggg cccgcatctg attagctagt tggtgagata acagcccacc    180
aaggcgacga tcagtagccg acctgagagg gtgatcggcc acattgggac tgagacacgg    240
cccaaactcc tacgggaggc agcagtgggg aatattgcac aatgggcgaa agcctgatgc    300
agcaacgccg cgtgaaggat gaagggtttc ggctcgtaaa cttctatcaa tagggaagaa    360
agaaatgacg gtacctaaat aagaagcccc ggctaactac gtgccagcag ccgcggtaat    420
acgtaggggg caagcgttat ccggaattac tgggtgtaaa gggagcgtag gcggcatggt    480
aagccagatg tgaaagcctt gggcttaacc cgaggattgc atttggaact atcaagctag    540
agtacaggag aggaaagcgg aattcctagt gtagcggtga aatgcgtaga tattaggaag    600
aacaccagtg gcgaaggcgg cttcctggac tgaaactgac gctgaggctc gaaagcgtgg    660
ggagcaaaca ggattagata ccctggtagt ccacgccgta acgatgagt gctaggtgtc    720
ggggaggaat cctcggtgcc gcagctaacg caataagcac tccacctggg gagtacgacc    780
gcaaggttga aactcaaagg aattgacggg gccccgcaca agcggtggag catgtggttt    840
aattcgaagc aacgcgaaga accttaccaa ggcttgacat cccgatgacc gctctagaga    900
tagagcttct cttcggagca tcggtgacag gtggtgcatg gttgtcgtca gctcgtgtcg    960
tgagatgttg ggttaagtcc cgcaacgagc gcaaccctta tcttcagtag ccatcattta   1020
gttgggcact ctggagagac tgccgtggat aacacggagg aaggtgggga tgacgtcaaa   1080
tcatcatgcc ccttatgtct tgggctacac acgtgctaca atggctggta acaaagtgac   1140
gcaaaacggc gacgttaagc aaatcacaaa aacccagtcc cagttcggat tgtagtctgc   1200
aactcgacta catgaagctg gaatcgctag taatcgcgaa tcagcatgtc gcggtgaata   1260
cgttcccggg ccttgtacac accgcccgtc acaccatggg agttggaagc acccgaagtc   1320
ggtgacctaa ccgtaaggaa ggagccgccg aaggtgaagc cagtgactgg ggtgaagtcg   1380
taacaaggta gccgtatcgg aaggtgcggc tggatcacct cctttt                  1425

<210> SEQ ID NO 10
<211> LENGTH: 1559
<212> TYPE: DNA
<213> ORGANISM: Lactobacillus salivarius

<400> SEQUENCE: 10
aatgagagtt tgatcctggc tcaggacgaa cgctggcggc gtgcctaata catgcaagtc     60
gaacgaaact ttcttacacc gaatgcttgc attcaccgta agaagttgag tggcggacgg    120
gtgagtaaca cgtgggtaac ctgcctaaaa gaagggata acacttggaa acaggtgcta    180
ataccgtata tctctaagga tcgcatgatc cttagatgaa agatggttct gctatcgctt    240
ttagatggac ccgcggcgta ttaactagtt ggtggggtaa cggcctacca aggtgatgat    300
acgtagccga actgagaggt tgatcggcca cattgggact gagacacggc ccaaactcct    360
acgggaggca gcagtaggga atcttccaca atggacgcaa gtctgatgga gcaacgccgc    420
gtgagtgaag aaggtcttcg gatcgtaaaa ctctgttgtt agagaagaac acgagtgaga    480
gtaactgttc attcgatgac ggtatctaac cagcaagtca cggctaacta cgtgccagca    540
```

```
gccgcggtaa tacgtaggtg gcaagcgttg tccggattta ttgggcgtaa agggaacgca    600
ggcggtcttt taagtctgat gtgaaagcct tcggcttaac cggagtagtg cattggaaac    660
tggaagactt gagtgcagaa gaggagagtg gaactccatg tgtagcggtg aaatgcgtag    720
atatatggaa gaacaccagt ggcgaaagcg gctctctggt ctgtaactga cgctgaggtt    780
cgaaagcgtg gtagcaaac aggattagat accctggtag tccacgccgt aaacgatgaa    840
tgctaggtgt tggagggttt ccgcccttca gtgccgcagc taacgcaata agcattccgc    900
ctggggagta cgaccgcaag gttgaaactc aaaggaattg acggggccc gcacaagcgg    960 tggagcatgt ggtttaattc gaagcaacgc gaagaacctt accaggtctt gacatccttt   1020
gaccacctaa gagattaggt tttcccttcg gggacaaagt gacaggtggt gcatggctgt   1080
cgtcagctcg tgtcgtgaga tgttgggtta agtcccgcaa cgagcgcaac ccttgttgtc   1140
agttgccagc attaagttgg gcactctggc gagactgccg gtgacaaacc ggaggaaggt   1200
ggggacgacg tcaagtcatc atgcccctta tgacctgggc tacacacgtg ctacaatgga   1260
cggtacaacg agtcgcaaga ccgcgaggtt tagctaatct cttaaagccg ttctcagttc   1320
ggattgtagg ctgcaactcg cctacatgaa gtcggaatcg ctagtaatcg cgaatcagca   1380
tgtcgcggtg aatacgttcc cgggccttgt acacaccgcc cgtcacacca tgagagtttg   1440
taacacccaa agccggtggg gtaaccgcaa ggagccagcc gtctaaggtg ggacagatga   1500
ttggggtgaa gtcgtaacaa ggtagccgta ggagaacctg cggctggatc acctcctttt   1559

<210> SEQ ID NO 11
<211> LENGTH: 1065
<212> TYPE: DNA
<213> ORGANISM: Lactobacillus reuteri

<400> SEQUENCE: 11
gtgacggtat ccaaccagaa agtcacggct aactacgtgc cagcagccgc ggtaatacgt     60
aggtggcaag cgttatccgg atttattggg cgtaaagcga cgcaggcgg ttgcttaggt    120 ctgatgtgaa agccttcggc ttaaccgaag aagtgcatcg gaaaccgggc gacttgagtg    180
cagaagagga cagtggaact ccatgtgtag cggtggaatg cgtagatata tggaagaaca    240
ccagtggcga aggcggctgt ctggtctgca actgacgctg aggctcgaaa gcatgggtag    300
cgaacaggat tagataccct ggtagtccat gccgtaaacg atgagtgcta ggtgttggag    360
ggtttccgcc cttcagtgcc ggagctaacg cattaagcac tccgcctggg gagtacgacc    420
gcaaggttga aactcaaagg aattgacggg gcccgcaca gcggtggag catgtggttt    480 aattcgaagc tacgcgaaga accttaccag gtcttgacat cttgcgctaa ccttagagat    540
aaggcgttcc cttcggggac gcaatgacag gtggtcatg tcgtcgtca gctcgtgtcg    600 tgagatgttg ggttaagtcc cgcaacgagc gcaacccttg ttactagttg ccagcattaa    660
gttgggcact ctagtgagac tgccggtgac aaaccggagg aaggtgggga cgacgtcaga    720
tcatcatgcc cctatgacc tgggctacac acgtgctaca atggacggta caacgagtcg    780
caagctcgcg agagtaagct aatctcttaa agccgttctc agttcggact gtaggctgca    840
actcgcctac acgaagtcgg aatcgctagt aatcgcggat cagcatgccg cggtgaatac    900
gttcccgggc cttgtacaca ccgcccgtca ccatggga gtttgtaacg cccaaagtcg    960
gtggcctaac ctttatggag ggagccgcct aaggcgggac agatgactgg ggtgaagtcg   1020
taacaaggta gccgtaggag aacctgcggc tggatcacct ccttt                   1065
```

```
<210> SEQ ID NO 12
<211> LENGTH: 52
<212> TYPE: DNA
<213> ORGANISM: Artificial Sequence
<220> FEATURE:
<223> OTHER INFORMATION: primer

<400> SEQUENCE: 12
tcgtcggcag cgtcagatgt gtataagaga caggtgccag cmgccgcggt aa          52

<210> SEQ ID NO 13
<211> LENGTH: 54
<212> TYPE: DNA
<213> ORGANISM: Artificial Sequence
<220> FEATURE:
<223> OTHER INFORMATION: primer

<400> SEQUENCE: 13
gtctcgtggg ctcggagatg tgtataagag acagggacta chvgggtwtc taat        54

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
cggtgaatac gttcycgg                                                18

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
ggwtaccttg ttacgactt                                               19

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
cttgtacaca ccgcccgtc                                               19

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cgcataacgt tgaaagatgg                                              20

<210> SEQ ID NO 18
<211> LENGTH: 19
<212> TYPE: DNA
<213> ORGANISM: Artificial Sequence
<220> FEATURE:
<223> OTHER INFORMATION: primer
```

```
<400> SEQUENCE: 18
ccttggtagg ccgttaccc                                              19

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19
tcatcattca accaaaggag caatcc                                      26

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
tggtgctgga ataaatgctt cat                                         23

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
tgcatcatct tttctttgaa ttgttc                                      26

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
atactataag ctatgaacaa cc                                          22
```

COMPOSITIONS FOR GUT HEALTH

CROSS-REFERENCE TO RELATED APPLICATIONS

This application is a U.S. National Stage Application under 35 U.S.C. § 371 of International Patent Application No. PCT/US2020/055937, filed Oct. 16, 2020, which claims priority to U.S. Provisional Patent Application No. 62/923,781, filed Oct. 21, 2019, the disclosure of each of which is incorporated herein in its entirety.

REFERENCE TO A SEQUENCE LISTING

The contents of the electronic submission of the text file Sequence Listing, named 20210315_NB41584WOPCT_SequenceListing.txt; was created on Mar. 15, 2021, and is 23,923 bytes in size, which is hereby incorporated by reference in its entirety.

FIELD OF THE INVENTION

Provided herein, inter alia, are multi-strain direct fed microbial bacterial consortia useful for improving animal gut health and/or performance as well as methods of making and using the same.

BACKGROUND

In monogastric animal species such as birds, the gastrointestinal tract and intestinal-associated microflora are not only involved in digestion and absorption but also interact with the immune and central nervous system to modulate health. The inside of the intestinal tract is coated with a thin layer of sticky, viscous mucous, and embedded in this mucus layer are millions and millions of bacteria and other microbes. When the intestinal bacteria are in balance (i.e., the good bacteria outnumber the bad bacteria), the gut is said to be healthy. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of "dysbiosis" or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota of poultry plays a significant role in the pathogenesis of many diseases and disorders, including a variety of pathogenic infections of the gut such as coccidiosis or necrotic enteritis.

Over the past several years, there has been increasing governmental and consumer pressure applied to the animal feed industry to decrease or curtail the use of antibiotics as components of animal nutrition feeding regimens. This pressure is due in large part to the recognition that use of such antibiotics contribute to the rise of antibiotic-resistant pathogenic microorganisms. However, this "No Antibiotics Ever" consumer trend, especially in the poultry industry, has led to the re-emergence of bacterial diseases, particularly necrotic enteritis (*Poultry Science*, Volume 97, Issue 6, 1 Jun. 2018, 1929-1933). Necrotic enteritis is caused by certain toxin-producing *Clostridium perfringens* strains. Under certain conditions *C. perfringens* produces toxins which cause lesions in the small intestines and ultimately result in reduced growth or death of the infected birds.

Accordingly, there is currently a recognized need for products and methods capable of reducing pathogenic bacterial populations in the digestive tracts of domesticated animals such as birds without the use of traditionally-used antibiotics.

The subject matter disclosed herein addresses these needs and provides additional benefits as well.

SUMMARY

Provided herein, inter alia, are multi-strain direct fed microbial bacterial consortia of short chain fatty acid (SCFA)-producing microorganisms and methods of making and using the same to inhibit pathogenic bacterial populations in the gastrointestinal tracts of an animal (such as birds, for example, chickens) and additionally promote improvement of one or more metrics in an animal such as increased bodyweight gain, decreased feed conversion ratio (FCR), improved gut barrier integrity, reduced mortality, reduced pathogen infection, and reduced pathogen shedding in feces.

Accordingly, in some aspects, provided herein are feed additive compositions comprising a direct fed microbial (DFM) comprising one or more biologically pure bacterial strains of *Anaerotruncus colihominis*. In some embodiments, the feed additive composition comprises one, two, three or four strains of *A. colihominis*. In some embodiments of any of the embodiments disclosed herein, the feed additive composition comprises a) a bacterial strain having a 16S ribosomal RNA sequence displaying at least 97.0% sequence similarity to a 16S ribosomal RNA sequence of a *Anaerotruncus colihominis* strain W1 deposited at Westerdijk Fungal Biodiversity Institute (WFDB) under number CBS 146120; b) a bacterial strain having a 16S ribosomal RNA sequence displaying at least 97.0% sequence similarity to a 16S ribosomal RNA sequence of a *Anaerotruncus colihominis* strain W2 deposited at Westerdijk Fungal Biodiversity Institute (WFDB) under number CBS 146122; c) a bacterial strain having a 16S ribosomal RNA sequence displaying at least 97.0% sequence similarity to a 16S ribosomal RNA sequence of a *Anaerotruncus colihominis* strain W3 deposited at Westerdijk Fungal Biodiversity Institute (WFDB) under number CBS 146123; and d) a bacterial strain having a 16S ribosomal RNA sequence displaying at least 97.0% sequence similarity to a 16S ribosomal RNA sequence of a *Anaerotruncus colihominis* strain W4 deposited at Westerdijk Fungal Biodiversity Institute (WFDB) under number CBS 146121. In some embodiments of any of the embodiments disclosed herein, the feed additive composition comprises a) *A. colihominis* strain W1 (CBS 146120) or a live strain having all of the identifying characteristics of *A. colihominis* strain W1 (CBS 146120); b) *A. colihominis* strain W2 (CBS 146122) or a live strain having all of the identifying characteristics of *A. colihominis* strain W2 (CBS 146122); c) *A. colihominis* strain W3 (CBS 146123) or a live strain having all of the identifying characteristics of *A. colihominis* strain W3 (CBS 146123); and d) *A. colihominis* strain W4 (CBS 146121) or a live strain having all of the identifying characteristics of *A. colihominis* strain W4 (CBS 146121) either (i) alone; or (ii) in combination with a culture supernatant derived from each of these strains. In some embodiments, the feed additive composition further comprises biologically pure bacterial strains of a) a *Coprococcus* sp.; b) *Clostridium lactatifermentans*; and c) *Pseudoflavonifractor capillosus*. In some embodiments, the feed additive composition comprises a) a bacterial strain having a 16S ribosomal RNA sequence displaying at least 97.0% sequence similarity to a 16S ribosomal RNA sequence of a *Coprococcus* sp. strain M1 deposited at Westerdijk Fungal Biodiversity Institute (WFDB) under number CBS 146125; b) a bacterial strain having a 16S ribosomal RNA sequence displaying at least 97.0% sequence similarity to a 16S ribosomal RNA sequence of a *Anaerotruncus colihominis* strain M2 deposited at Westerdijk Fungal Biodiversity Institute (WFDB) under number CBS 146119; c) a bacterial strain having a 16S ribosomal RNA sequence displaying at least 97.0% sequence similarity to a 16S ribosomal RNA sequence of a *Clostridium lactatifermentans* strain M3 deposited at Westerdijk Fungal Biodiversity Institute (WFDB) under number CBS 146124; and d) a bacterial strain having a 16S ribosomal RNA sequence displaying at least 97.0% sequence similarity to a 16S ribosomal RNA sequence of a *Pseudoflavonifractor capillosus* strain M4. In some embodiments of any of the embodiments disclosed herein, the feed additive composition comprises a) *Coprococcus* sp. strain M1 (CBS 146125) or a live strain having all of the identifying characteristics of *Coprococcus* sp. strain M1 (CBS 146125); b) *A. colihominis* strain M2 (CBS 146119) or a live strain having all of the identifying characteristics of *A. colihominis* strain M2 (CBS 146119); c) *C. lactatifermentans* strain M3 (CBS 146124) or a live strain having all of the identifying characteristics of *C. lactatifermentans* strain M3 (CBS 146124); and d) a *P. capillosus* strain either (i) alone; or (ii) in combination with a culture supernatant derived from each of these strains.

In other aspects, provided herein is a feed additive composition comprising a direct fed microbial (DFM) comprising one or more biologically pure bacterial strains of a short chain fatty acid (SCFA)-producing bacterial strain and one or more biologically pure lactic acid producing bacterial strains. In some embodiments, the feed additive composition comprises a) a biologically pure strain of *Clostridium lactatifermentans*; and b) two biologically pure lactic acid producing bacterial strains. In some embodiments of any of the embodiments disclosed herein, the two biologically pure lactic acid producing bacterial strains are *Lactobacillus salivarius* and *Lactobacillus reuteri*. In some embodiments of any of the embodiments disclosed herein, the feed additive composition comprises a) a bacterial strain having a 16S ribosomal RNA sequence displaying at least 97.0% sequence similarity to a 16S ribosomal RNA sequence of a *Clostridium lactatifermentans* strain 2F1 deposited at Westerdijk Fungal Biodiversity Institute (WFDB) under number 146124; b) a bacterial strain having a 16S ribosomal RNA sequence displaying at least 97.0% sequence similarity to a 16S ribosomal RNA sequence of a *Lactobacillus salivarius* strain 2F2 deposited at Westerdijk Fungal Biodiversity Institute (WFDB) under number CBS 146126; and c) a bacterial strain having a 16S ribosomal RNA sequence displaying at least 97.0% sequence similarity to a 16S ribosomal RNA sequence of a *Lactobacillus reuteri* strain 2F3 deposited at Westerdijk Fungal Biodiversity Institute (WFDB) under number CBS 145921. In some embodiments of any of the embodiments disclosed herein, the feed additive composition comprises a) *C. lactatifermentans* strain 2F1 (CBS 146124) or a live strain having all of the identifying characteristics of *C. lactatifermentans* strain 2F1 (CBS 146124); b) *L. salivarius* strain 2F2 (CBS 146126) or a live strain having all of the identifying characteristics of *L. salivarius* strain 2F2 (CBS 146126); and c) *L. reuteri* strain 2F3 (CBS 145921) or a live strain having all of the identifying characteristics of *L. reuteri* strain 2F3 (CBS 145921) either (i) alone; or (ii) in combination with a culture supernatant derived from each of these strains. In some embodiments of any of the embodiments disclosed herein a) the 16S ribosomal RNA sequence of *Anaerotruncus colihominis* strain W1 comprises the nucleotide sequence of SEQ ID NO:1; b) the 16S ribosomal RNA sequence of *Anaerotruncus colihominis* strain W2 comprises the nucleotide sequence of SEQ ID NO:2; c) the 16S ribosomal RNA sequence of *Anaerotruncus colihominis* strain W3 comprises the nucleotide sequence of SEQ ID NO:3; and d) the 16S ribosomal RNA sequence of *Anaerotruncus colihominis* strain W4 comprises the nucleotide sequence of SEQ ID NO:4. In some embodiments of any of the embodiments disclosed herein a) the 16S ribosomal RNA sequence of *Coprococcus* sp. strain M1 comprises the nucleotide sequence of SEQ ID NO:5; b) the 16S ribosomal RNA sequence of *Anaerotruncus colihominis* strain M2 comprises the nucleotide sequence of SEQ ID NO:6; c) the 16S ribosomal RNA sequence of *Clostridium lactatifermentans* strain M3 comprises the nucleotide sequence of SEQ ID NO:7; and d) the 16S ribosomal RNA sequence of *Pseudoflavonifractor capillosus* strain M4 comprises the nucleotide sequence of SEQ ID NO:8. In some embodiments of any of the embodiments disclosed herein a) the 16S ribosomal RNA sequence of *Clostridium lactatifermentans* strain 2F1 comprises the nucleotide sequence of SEQ ID NO:9; b) the 16S ribosomal RNA sequence of *Lactobacillus salivarius* strain 2F2 comprises the nucleotide sequence of SEQ ID NO:10; and c) the 16S ribosomal RNA sequence of *Lactobacillus reuteri* strain 2F3 comprises the nucleotide sequence of SEQ ID NO:11. In some embodiments of any of the embodiments disclosed herein, the composition produces one or more short chain fatty acids selected from the group consisting of butyrate, isobutyrate, propionate, acetate, isovalerate, and valerate. In some embodiments of any of the embodiments disclosed herein, the feed additive composition further comprises one or more enzymes. In some embodiments, the one or more enzymes are selected from the group consisting of a phytase, a protease, an amylase, a xylanase and a beta-glucanase. In some embodiments of any of the embodiments disclosed herein, each strain is present at a concentration of at least about $1 \times 10^3$ CFU/g feed additive composition to at least about $1 \times 10^9$ CFU/g feed additive composition. In some embodiments of any of the embodiments disclosed herein, the composition inhibits at least one pathogen selected from avian pathogenic *Salmonella* sp., *Escherichia coli*, *Clostridium perfringens* and Enterobacteriaceae in a gastrointestinal tract of a bird having ingested an effective amount of said direct fed microbial composition.

In further aspects, provided herein is a premix comprising any of the feed additive compositions disclosed herein and at least one mineral and/or at least one vitamin. In still other aspects, provided herein is a feed or feedstuff comprising any of the feed additive compositions disclosed herein or any of the premixes disclosed herein.

In another aspect, provided herein are kits comprising a) any of the feed additive compositions disclosed herein; and b) written instructions for administration to an animal. In some embodiments, the kit further comprises one or more enzymes. In some embodiments, the one or more enzymes are selected from the group consisting of a phytase, a protease, an amylase, a xylanase and a beta-glucanase.

In further aspects, provided herein is a method for improving one or more metrics in an animal selected from the group consisting of increased bodyweight gain, intestinal health status, decreased feed conversion ratio (FCR), improved gut barrier integrity, reduced mortality, reduced pathogen infection, and reduced pathogen shedding in feces comprising administering an effective amount of any of the feed additive compositions disclosed herein, any of the premixes disclosed herein, or any of the feeds or feedstuffs disclosed herein to the animal, thereby improving the one or more metrics in the animal. In some embodiments, the feed additive composition increases one or more of the acetate, isobutyrate, butyrate, isovalerate, and/or valerate content of the gastrointestinal tract of the animal. In some embodiments of any of the embodiments disclosed herein, the feed additive composition increases the butyrate content of the gastrointestinal tract of the animal. In some embodiments of any of the embodiments disclosed herein, the pathogen is one or more of *Clostridium perfringens, Campylobacter jejuni*, Enterobacteriaceae, a *Salmonela* sp., and/or *Escherichia coli*. In some embodiments of any of the embodiments disclosed herein, the method further treats, prevents, or decreases incidence of necrotic enteritis. In some embodiments of any of the embodiments disclosed herein, the animal is a domesticated bird. In some embodiments, the domesticated bird is selected from the group consisting of chickens, turkeys, ducks, geese, quail, emus, ostriches, and pheasant. In some embodiments, the chicken is a broiler or a layer.

In other aspects, provided herein is a method for preparing a feed additive composition comprising combining a) a bacterial strain having a 16S ribosomal RNA sequence displaying at least 97.0% sequence similarity to a 16S ribosomal RNA sequence of a *Anaerotruncus colihominis* strain W1 deposited at CBS under number CBS 146120; b) a bacterial strain having a 16S ribosomal RNA sequence displaying at least 97.0% s sequence similarity to a 16S ribosomal RNA sequence of a *Anaerotruncus colihominis* strain W2 deposited at CBS under number CBS 146122; c) a bacterial strain having a 16S ribosomal RNA sequence displaying at least 97.0% sequence similarity to a 16S ribosomal RNA sequence of a *Anaerotruncus colihominis* strain W3 deposited at CBS under number CBS 146123; and d) a bacterial strain having a 16S ribosomal RNA sequence displaying at least 97.0% sequence similarity to a 16S ribosomal RNA sequence of a *Anaerotruncus colihominis* strain W4 deposited at CBS under number CBS 146121. In some embodiments a) the *A. colihominis* strain W1 is an *A. colihominis* strain W1 (CBS 146120) or a live strain having all of the identifying characteristics of *A. colihominis* strain W1 (CBS 146120); b) the *A. colihominis* strain W2 is an *A. colihominis* strain W2 (CBS 146122) or a live strain having all of the identifying characteristics of *A. colihominis* strain W2 (CBS 146122); c) the *A. colihominis* strain W3 is an *A. colihominis* strain W3 (CBS 146123) or a live strain having all of the identifying characteristics of *A. colihominis* strain W3 (CBS 146123); and d) the *A. colihominis* strain W4 is an *A. colihominis* strain W4 (CBS 146121) or a live strain having all of the identifying characteristics of *A. colihominis* strain W4 (CBS 146121) either (i) alone; or (ii) in combination with a culture supernatant derived from each of these strains.

In still other aspects, provided herein is a method for preparing a feed additive composition comprising combining a) a bacterial strain having a 16S ribosomal RNA sequence displaying at least 97.0% sequence similarity to a 16S ribosomal RNA sequence of a *Coprococcus* sp. strain M1 deposited at CBS under number CBS 146125; b) a bacterial strain having a 16S ribosomal RNA sequence displaying at least 97.0% sequence similarity to a 16S ribosomal RNA sequence of a *Anaerotruncus colihominis* strain M2 deposited at CBS under number CBS 146119; c) a bacterial strain having a 16S ribosomal RNA sequence displaying at least 97.0% sequence similarity to a 16S ribosomal RNA sequence of a *Clostridium lactatifermentans* strain M3 deposited at CBS under number CBS 146124; and d) a bacterial strain having a 16S ribosomal RNA sequence displaying at least 97.0% sequence similarity to a 16S ribosomal RNA sequence of a *Pseudoflavonifractor capillosus* strain M4. In some embodiments, the a) *Coprococcus* sp. strain M1 is an *Coprococcus* sp. strain M1 (CBS 146125) or a live strain having all of the identifying characteristics of *Coprococcus* sp. strain M1 (CBS 146125); b) the *A. colihominis* strain M2 is an *A. colihominis* strain M2 (CBS 146119) or a live strain having all of the identifying characteristics of *A. colihominis* strain M2 (CBS 146119); and c) the *C. lactatifermentans* strain M3 is a *C. lactatifermentans* strain M3 (CBS 146124) or a live strain having all of the identifying characteristics of *C. lactatifermentans* strain M3 (CBS 146124) either (i) alone; or (ii) in combination with a culture supernatant derived from each of these strains.

In still other aspects, provided herein is a method for preparing a feed additive composition comprising combining a) a bacterial strain having a 16S ribosomal RNA sequence displaying at least 97.0% sequence similarity to a 16S ribosomal RNA sequence of a *Clostridium lactatifermentans* strain 2F1 deposited at CBS under number CBS 146124; b) a bacterial strain having a 16S ribosomal RNA sequence displaying at least 97.0% s sequence similarity to a 16S ribosomal RNA sequence of a *Lactobacillus salivarius* strain 2F2 deposited at CBS under number CBS 146126; and c) a bacterial strain having a 16S ribosomal RNA sequence displaying at least 97.0% sequence similarity to a 16S ribosomal RNA sequence of a *Lactobacillus reuteri* strain 2F3 deposited at CBS under number CBS 145921. In some embodiments a) the *C. lactatifermentans* strain 2F1 is an *C. lactatifermentans* strain W1 (CBS 146124) or a live strain having all of the identifying characteristics of *C. lactatifermentans* strain 2F1 (CBS 146124); b) the *L. salivarius* strain 2F2 is an *L. salivarius* strain 2F2 (CBS 146126) or a live strain having all of the identifying characteristics of *L. salivarius* strain 2F2 (CBS 146126); and c) the *L. reuteri* strain 2F3 is an *L. reuteri* strain 2F3 (CBS 145921) or a live strain having all of the identifying characteristics of *L. reuteri* strain 2F3 (CBS 145921) either (i) alone; or (ii) in combination with a culture supernatant derived from each of these strains. In some embodiments of any of the embodiments disclosed herein, the method further comprises combining one or more enzyme with the feed additive composition. In some embodiments, the one or more enzymes are selected from the group consisting of a phytase, a protease, an amylase, a xylanase and a beta-glucanase. In some embodiments of any of the embodiments disclosed herein, at least about $1 \times 10^3$ CFU/g feed additive composition to at least about $1 \times 10^9$ CFU/g feed additive composition is combined to form the feed additive composition. In some embodiments of any of the embodiments disclosed herein, the method further comprises packaging the feed additive composition.

In another aspect, provided herein is a method for preparing a premix comprising combining any of the feed additive compositions disclosed herein with at least one mineral and/or at least one vitamin. In some embodiments, the method further comprises comprising packaging the premix.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

DETAILED DESCRIPTION

Figure 1A:
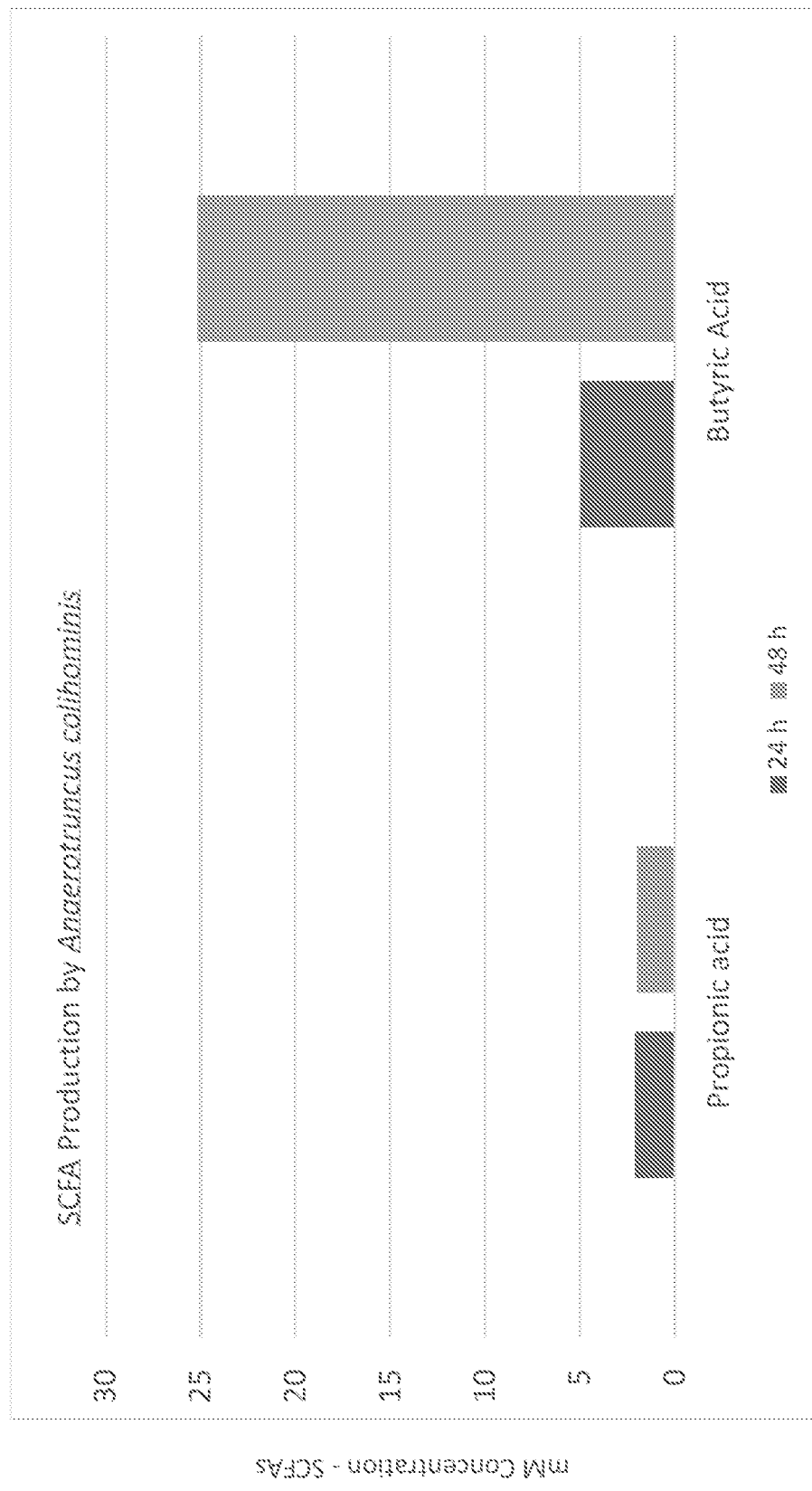
FIG. 1A depicts a bar graph showing short chain fatty acid (SCFA) production by *Anaerotruncus colihominis* in culture at 24 and 48 hours.

A variety of microbial species have been shown to have certain degrees of efficacy against gut pathogens either in vitro or in vivo. Commonly studied organisms have included *Bacillus* or *Lactobacillus*. Another group of microbes of potential interest are obligate anaerobes that can produce short-chain fatty acids (SCFAs). SCFAs, for example, propionate and butyrate (i.e. the conjugate bases of propionic and butyric acid, respectively), are suspected to have many beneficial properties for gut health (see, e.g., *Adv Immunol*. 2014; 121:91-119; *Eur J Pharmacol*. 2018 Jul. 15; 831:52-59; *Adv Nutr*. 2019 Jan. 1; 10(suppl_1):S49-S66).

As described in more detail herein, the inventors have surprisingly discovered that administering specific species of SCFA-producing microbes to animals (such as domesticated birds, for example, chickens) can improve performance on one or more metrics that include increased bodyweight gain, intestinal health status, decreased feed conversion ratio (FCR), improved gut barrier integrity, reduced mortality, reduced pathogen infection (such as, but not limited to, infection by *Clostridium perfringens*), and reduced pathogen shedding in feces. Without being bound to theory, it is believed that SCFAs play an important role in the prevention of intestinal inflammation and in the maintenance of intestinal homeostasis. While many obligate anaerobes have the capability to produce SCFAs, not all species can provide benefits to animals when administered as a feed additive or as part of a feed. However, as will be described in the Examples section, administration of particular combinations of microbials was discovered to be surprisingly effective in the prevention and/or treatment of gut pathogenesis in animals as well as maintenance of overall health.

I. Definitions

Short-chain fatty acids (SCFAs) (also referred to as volatile fatty acids (VFAs)), as used herein, are fatty acids with less than six carbon atoms. Non-limiting examples of SCFAs include, formic acid (methanoic acid), acetic acid (ethanoic acid), propionic acid (propanoic acid), butanoic acid (butyric acid), isobutyric acid (2-methylpropanoic acid), valeric acid (pentanoic acid), and isovaleric acid (3-methylbutanoic acid). Inclusive in this definition of SCFAs are also the conjugate bases of SCFAs including, without limitation, formate, acetate, propionate, butyrate, isobutyrate, valerate, and isovalerate.

As used herein, "microorganism" or "microbe" refers to a bacterium, a fungus, a virus, a protozoan, and other microbes or microscopic organisms.

As used here in the term "direct fed microbial" refers to a composition for consumption by animals (i.e. as an or as a component of animal feed) that contains viable microorganisms, i.e. microorganisms that are capable of living and reproducing. See, for example, U.S. Pat. No. 8,420,074. A direct fed microbial may comprise one or more (such as any of 1, 2, 3, 4, 5, or 6 or more) of any of the microbial strains described herein.

A bacterial "strain" as used herein refers to a bacterium which remains genetically unchanged when grown or multiplied. The multiplicity of identical bacteria is included.

By "at least one strain," is meant a single strain but also mixtures of strains comprising at least two strains of microorganisms. By "a mixture of at least two strains," is meant a mixture of two, three, four, five, six or even more strains. In some embodiments of a mixture of strains, the proportions can vary from 1% to 99%. When a mixture comprises more than two strains, the strains can be present in substantially equal proportions in the mixture or in different proportions.

For purposes of this disclosure, a "biologically pure strain" means a strain containing no other bacterial strains in quantities sufficient to interfere with replication of the strain or to be detectable by normal bacteriological techniques. "Isolated" when used in connection with the organisms and cultures described herein includes not only a biologically pure strain, but also any culture of organisms which is grown or maintained other than as it is found in nature. In some embodiments, the strains are mutants, variants, or derivatives of strains W1, W2, W3, W4, M1, M2, M3, M4, 2F1, 2F2 and 2F3 that also provide benefits comparable to that provided by W1, W2, W3, W4, M1, M2, M3, M4, 2F1, 2F2 and 2F3. In some embodiments, the strains are strains having all of the identifying characteristics of strains W1, W2, W3, W4, M1, M2, M3, M4, 2F1, 2F2 and 2F3. Further, each individual strain (W1, W2, W3, W4, M1, M2, M3, M4, 2F1, 2F2 and 2F3) or any combination of these strains can also provide one or more of the benefits described herein. It will also be clear that addition of other microbial strains, carriers, additives, enzymes, yeast, or the like will also provide one or more benefits or improvement of one or more metrics in an animal and will not constitute a substantially different DFM.

The term "16S rRNA" or "16S ribosomal RNA" means the rRNA constituting the small subunit of prokaryotic ribosomes. In bacteria, this sequence can be used to identify and characterize operational taxonomic units.

The term "sequence identity" or "sequence similarity" as used herein, means that two polynucleotide sequences, a candidate sequence and a reference sequence, are identical (i.e. 100% sequence identity) or similar (i.e. on a nucleotide-by-nucleotide basis) over the length of the candidate sequence. In comparing a candidate sequence to a reference sequence, the candidate sequence may comprise additions or deletions (i.e. gaps) as compared to the reference sequence (which does not comprise additions or deletions) for optimal alignment of the two sequences. Optimal alignment of sequences for determining sequence identity may be conducted using the any number of publicly available local alignment algorithms known in the art such as ALIGN or Megalign (DNASTAR), or by inspection.

The term "percent (%) sequence identity" or "percent (%) sequence similarity," as used herein with respect to a reference sequence is defined as the percentage of nucleotide residues in a candidate sequence that are identical to the residues in the reference polynucleotide sequence after optimal alignment of the sequences and introducing gaps, if necessary, to achieve the maximum percent sequence identity.

As used herein, "prevent," "preventing," "prevention" and grammatical variations thereof refers to a method of partially or completely delaying or precluding the onset or recurrence of a disorder or condition (such as necrotic enteritis) and/or one or more of its attendant symptoms or barring an animal from acquiring or reacquiring a disorder or condition or reducing an animal's risk of acquiring or reacquiring a disorder or condition or one or more of its attendant symptoms.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

The term "poultry," as used herein, means domesticated birds kept by humans for their eggs, their meat or their feathers. These birds are most typically members of the superorder Galloanserae, especially the order Galliformes which includes, without limitation, chickens, quails, ducks, geese, emus, ostriches, pheasant, and turkeys.

As used herein "administer" or "administering" is meant the action of introducing one or more microbial strain, an exogenous feed enzyme and/or a strain and an exogenous feed enzyme to an animal, such as by feeding or by gavage.

As used herein, "effective amount" means a quantity of DFM and/or exogenous enzymes to improve one or more metrics in an animal. Improvement in one or more metrics of an animal (such as, without limitation, any of increased bodyweight gain, intestinal health status, decreased feed conversion ratio (FCR), improved gut barrier integrity, reduced mortality, reduced pathogen infection, and reduced pathogen shedding in feces) can be measured as described herein or by other methods known in the art. An effective amount can be administered to the animal by providing ad libitum access to feed containing the DFM and exogenous enzymes. The DFM and exogenous enzymes can also be administered in one or more doses.

The term "intestinal health status" refers to the status of the gut wall structure and morphology which can be affected by, for example, infectious agents or a non-infectious cause, such as a suboptimal formulated diet. "Gut wall structure and morphology" or "gut barrier integrity" can refer to, without limitation, epithelial damage and epithelial permeability which is characterized by a shortening of villi, a lengthening of crypts and an infiltration of inflammatory cells (such as, without limitation, CD3+ cells). The latter damage and inflammation markers can also be associated with a "severe" macroscopic appearance of the gut—compared to a "normal" appearance—when evaluated using a scoring system such as the one described by Teirlynck et al. (2011).

As used herein, the term "feed" is used synonymously herein with "feedstuff." Feed broadly refers to a material, liquid or solid, that is used for nourishing an animal, and for sustaining normal or accelerated growth of an animal including newborns or young and developing animals. The term includes a compound, preparation, mixture, or composition suitable for intake by an animal (such as, e.g., for poultry such as quail, ducks, turkeys, and chickens). In some embodiments, a feed or feed composition comprises a basal food composition and one or more feed additives or feed additive compositions. The term "feed additive" as used herein refers to components included for purposes of fortifying basic feed with additional components to promote feed intake, treat or prevent disease, or alter metabolism. Feed additives include pre-mixes.

A "premix," as referred to herein, may be a composition composed of micro-ingredients such as, but not limited to, one or more of vitamins, minerals, chemical preservatives, antibiotics, fermentation products, and other essential ingredients. Premixes are usually compositions suitable for blending into commercial rations.

As used herein, "improving one or more metrics in an animal" refers to improvements on measurements relevant to the growth and/or health of an animal (such as a domesticated bird, for example, a chicken), measured by one or more of the following parameters: average daily weight gain (ADG), overall weight, mortality, feed conversion (which includes both feed: gain and gain: feed), feed intake, intestinal health status, decreased feed conversion ratio (FCR), improved gut barrier integrity, reduced mortality, reduced pathogen infection, and reduced pathogen shedding in feces. "An improvement in a metric" or "improved metric" as used herein, refers to an improvement in at least one of the parameters listed under the metrics in an animal definition.

As used herein, the term "feed conversion ratio" refers to the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, in connection with a numerical value, the term "about" refers to a range of −10% to +10% of the numerical value, unless the term is otherwise specifically defined in context.

As used herein, the singular terms "a," "an," and "the" include the plural reference unless the context clearly indicates otherwise.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is also noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) can further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art to which this invention pertains.

Other definitions of terms may appear throughout the specification.

II. Compositions

A. Strains

Direct fed microbials (DFMs) refers to the feeding of beneficial microbes to animals, such as domestic birds when they are under periods of stress (disease, ration changes, environmental or production challenges) or as a part of a daily nutritional regimen to prevent disease and facilitate nutrient usage during digestion. Probiotics is another term for this category of feed additives. Probiotics or DFMs have been shown to improve animal performance in controlled studies. In some embodiments, DFMs include both direct fed bacteria and/or yeast-based products and, in particular embodiments, include viable microorganisms. The term "viable microorganism" means a microorganism which is metabolically active or able to differentiate.

In one embodiment, the DFM may be a spore forming bacterium and hence the term DFM may refer to a composition that is comprised of or contain spores, e.g., bacterial spores. Therefore, in one embodiment the term "viable microorganism" as used herein may include microbial spores, such as endospores or conidia. In another embodiment, the DFM in the feed additive composition according to the present invention is not comprised of or does not contain microbial spores, e.g. endospores or conidia (i.e., the DFM is non-spore forming).

The strains provided herein include *Anaerotruncus colihominis* strain W1, *Anaerotruncus colihominis* strain W2, *Anaerotruncus colihominis* strain W3, *Anaerotruncus colihominis* strain W4, *Coprococcus* sp. strain M1, *Anaerotruncus colihominis* strain M2, *Clostridium lactatifermentans* strain M3, *Pseudoflavonifractor capillosus* strain M4, *Clostridium lactatifermentans* strain 2F1, *Lactobacillus salivarius* strain 2F2, and *Lactobacillus reuteri* strain 2F3 which are also referred to herein as W1, W2, W3, W4, M1, M2, M3, M4, 2F1, 2F2, and 2F3, respectively.

*Anaerotruncus colihominis* strain W1, *Anaerotruncus colihominis* strain W2, *Anaerotruncus colihominis* strain W3, and *Anaerotruncus colihominis* strain W4 were deposited on Oct. 9, 2019 at the Westerdijk Fungal Biodiversity Institute (WFDB), Uppsalalaan 8, 3584 CT, Utrecht, The Netherlands and given accession numbers CBS 146120, CBS 146122, CBS 146123, and CBS 146121, respectively.

The deposits were made under the provisions of the Budapest Treaty on the International Recognition of the Deposit of Microorganisms for the Purposes of Patent Procedure. One or more strain provided herein can be used as a direct-fed microbial (DFM).

*Coprococcus* sp. strain M1, *Anaerotruncus colihominis* strain M2, and *Clostridium lactatifermentans* strain M3, were deposited on Oct. 9, 2019 at the Westerdijk Fungal Biodiversity Institute (WFDB), Uppsalalaan 8, 3584 CT, Utrecht, The Netherlands and given accession numbers CBS 146125, CBS 146119, and CBS 146124, respectively. The deposits were made under the provisions of the Budapest Treaty on the International Recognition of the Deposit of Microorganisms for the Purposes of Patent Procedure. One or more strain provided herein can be used as a direct-fed microbial (DFM).

*Clostridium lactatifermentans* strain 2F1, *Lactobacillus salivarius* strain 2F2, and *Lactobacillus reuteri* strain 2F3 were deposited on Jul. 24, 2019 and Oct. 9, 2019 at the Westerdijk Fungal Biodiversity Institute (WFDB), Uppsalalaan 8, 3584 CT, Utrecht, The Netherlands and given accession numbers CBS 146124, CBS 146126, and CBS 145921, respectively. The deposits were made under the provisions of the Budapest Treaty on the International Recognition of the Deposit of Microorganisms for the Purposes of Patent Procedure. One or more strain provided herein can be used as a direct-fed microbial (DFM). Multiple strains of direct fed microbials can be combined into a single composition (for example, a feed additive composition or a feed) to form a multi-strain DFM.

DFM compositions can include those that contain one or more strains (such as any of about 1, 2, 3, 4, 5, 6, 7, or 8 or more strains) of *Anaerotruncus colihominis*. This microbe is a gram-positive, non-spore-forming, rod-shaped and anaerobic bacterium from the genus of *Anaerotruncus* which has been observed to occur in human feces (Lau et al., *J Clin Pathol.* 2006 July; 59(7): 748-752).

The DFM composition can include one or more of *A. colihominis* strains W1, W2, W3, and/or W4 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *A. colihominis* strains W1 (SEQ ID NO:1), W2 (SEQ ID NO:2), W3 (SEQ ID NO:3), and/or W4 (SEQ ID NO:4). In some embodiments, the DFM composition includes only *A. colihominis* strain W1, W2, W3, or W4. In another embodiment, DFM composition includes *A. colihominis* strains W1 and W2; *A. colihominis* strains W1 and W3; *A. colihominis* strains W1 and W4; *A. colihominis* strains W2 and W3; *A. colihominis* strains W2 and W4; *A. colihominis* strains W3 and W4; *A. colihominis* strains W1, W2, and W3; *A. colihominis* strains W1, W3, and W4; *A. colihominis* strains W2, W3, and W4; or *A. colihominis* strains W1, W2, W3, and W4. Additionally, when cultured together, one or more *A. colihominis* strains W1, W2, W3, and/or W4 have one or more physiological or metabolic properties that individually cultured *A. colihominis* strains lack. These properties can include, without limitation, changes in the amount and/or type of short chain fatty acid produced, change in metabolic profile, and/or a change in the composition of media in which the bacteria are cultured together (such as butyric acid).

The DFM compositions provided herein can include one or more of *A. colihominis* strains W1, W2, W3, and/or W4 (i.e. the compositions include the actual bacteria from these strains) and/or one or more culture supernatants derived from the culturing of these strains (individually or in co-culture).

DFM compositions can additionally include those that contain one or more of *Coprococcus* sp. microbes, *Anaerotruncus colihominis* microbes, *Clostridium lactatifermentans* microbes, and/or *Pseudoflavonifractor capillosus* microbes. *Coprococcus* is a genus of gram-positive anaerobic cocci which has been observed in the human faecal flora. The genus is bio-chemically closely related to Ruminococcus and phylogenetically to the genus *Lachnospira*. *Clostridium lactatifermentans* is a gram positive rod-shaped bacterium with tapered ends showing no motility and no spore formation (van der Wielen et al., *Int J Syst Evol Microbiol*. 2002 May; 52(Pt 3):921-5). *Pseudoflavonifractor capillosus* is a normal gram-negative resident of the healthy human gut. In one comprehensive 16S rDNA sequence-based enumeration of the colonic microbiota of three healthy adult humans it represented, on average, 0.008% of all 16S rDNA sequences and 0.016% of the sequences in its division (Eckburg et. al. *Science*. 2005 Jun. 10; 308(5728):1635-8)). It is also associated with human cysts and wounds, and been known to cause neonatal sepsis.

The DFM composition can include one or more of *Coprococcus* sp. strain M1, *A. colihominis* strain M2, *C. lactatifermentans* strain M3, and/or a *P. capillosus* strain (such as *P. capillosus* strain M4) or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *Coprococcus* sp. strain M1 (SEQ ID NO:5), *A. colihominis* strain M2 (SEQ ID NO:6), *C. lactatifermentans* strain M3 (SEQ ID NO:7), and/or *P. capillosus* strain M4 (SEQ ID NO:8). In some embodiments, the DFM composition includes only *Coprococcus* sp. strain M1, *A. colihominis* strain M2, *C. lactatifermentans* strain M3, or a *P. capillosus* strain (such as *P. capillosus* strain M4). In another embodiment, the DFM composition includes *Coprococcus* sp. strain M1 and *A. colihominis* strain M2; *Coprococcus* sp. strain M1 and *C. lactatifermentans* strain M3; *Coprococcus* sp. strain M1 and a *P. capillosus* strain (such as *P. capillosus* strain M4); *A. colihominis* strains M2 and *C. lactatifermentans* strain M3; *A. colihominis* strain M2 and a *P. capillosus* strain (such as *P. capillosus* strain M4); *C. lactatifermentans* strain M3 and a *P. capillosus* strain (such as *P. capillosus* strain M4); *Coprococcus* sp. M1, *A. colihominis* strain M2, and *C. lactatifermentans* strain M3; *Coprococcus* sp. strain M1, *C. lactatifermentans* strain M3, and a *P. capillosus* strain (such as *P. capillosus* strain M4); *A. colihominis* strain M2, *C. lactatifermentans* strain M3, and a *P. capillosus* strain a (such as *P. capillosus* strain M4); or *Coprococcus* sp. strain M1, *A. colihominis* strain M2, *C. lactatifermentans* strain M3, and a *P. capillosus* strain (such as *P. capillosus* strain M4). Additionally, when cultured together, one or more *Coprococcus* sp. strain M1, *A. colihominis* strain M2, *C. lactatifermentans* strain M3, and/or a *P. capillosus* strain (such as *P. capillosus* strain M4) have one or more physiological or metabolic properties that individually cultured strains lack. These properties can include, without limitation, changes in the amount and/or type of short chain fatty acid production (such as the production of valeric acid which is only observed when these microbes are cultured together).

The DFM compositions provided herein can include one or more *Coprococcus* sp. strain M1, *A. colihominis* strain M2, *C. lactatifermentans* strain M3, and/or a *P. capillosus* strain (such as *P. capillosus* strain M4) (i.e. the compositions include the actual bacteria from these strains) and/or one or more culture supernatants derived from the culturing of these strains (individually or in co-culture).

DFM compositions provided herein can additionally include those that contain one or more of *Clostridium lactatifermentans* microbes, *Lactobacillus salivarius* microbes, and/or *Lactobacillus reuteri* microbes. *Clostridium lactatifermentans* is a gram positive rod-shaped bacterium with tapered ends showing no motility and no spore formation (van der Wielen et al., *Int J Syst Evol Microbiol*. 2002 May; 52(Pt 3):921-5). *Lactobacillus salivarius* is a lactic acid bacteria which is part of the indigenous microbiota of humans and hamsters (Raftis et al., *Appl. Environ. Microbiol*. Jan 2011, 77 (3) 954-965). There has been a recent increase in the number of studies in which the probiotic utility of diverse *L. salivarius* strains was explored (Neville & O'Toole, *Future Microbiol*. 2010, 5:759-774). *Lactobacillus reuteri* is a gram-positive bacterium that naturally inhabits the gut of mammals and birds.

The DFM composition can include one or more of *C. lactatifermentans* strain 2F1, *L. salivarius* strain 2F2, and/or *L. reuteri* strain 2F3 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *C. lactatifermentans* strain 2F1 (SEQ ID NO:9), *L. salivarius* strain 2F2 (SEQ ID NO:10), and/or *L. reuteri* strain 2F3 (SEQ ID NO:11). In some embodiments, the DFM composition includes only *C. lactatifermentans* strain 2F1, *L. salivarius* strain 2F2, or *L. reuteri* strain 2F3. In another embodiment, the DFM composition includes *C. lactatifermentans* strain 2F1 and *L. salivarius* strain 2F2; *C. lactatifermentans* strain 2F1 and *L. reuteri* strain 2F3; *L. salivarius* strain 2F2 and *L. reuteri* strain 2F3; *C. lactatifermentans* strain 2F1, *L. salivarius* strain 2F2, and *L. reuteri* strain 2F3. Additionally, when cultured together, one or more *C. lactatifermentans* strain 2F1, *L. salivarius* strain 2F2, and/or *L. reuteri* strain 2F3 have one or more physiological or metabolic properties that individually cultured strains lack. These properties can include, without limitation, changes in the amount and/or type of short chain fatty acid produced (such as the production of lactic acid which is only observed when these microbes are cultured together) change in metabolic profile, and/or a change in the composition of media in which the bacteria are cultured together.

The DFM compositions provided herein can include one or more *C. lactatifermentans* strain 2F1, *L. salivarius* strain 2F2, and *L. reuteri* strain 2F3 (i.e. the compositions include the actual bacteria from these strains) and/or one or more culture supernatants derived from the culturing of these strains (individually or in co-culture).

B. Exogenous Enzymes

Supplemental enzymes can be used as additives to animal feed, particularly poultry and swine feeds, as a means to improve nutrient utilization and performance characteristics.

In one embodiment, the disclosure relates to a composition comprising one or more DFM (such as DFMs containing any of the microbial strains disclosed herein) and one or more exogenous feed enzymes. In another embodiment, the disclosure relates to a composition comprising, consisting of, or consisting essentially of a multi-strain DFM (such as any of the multi-strain DFM compositions disclosed herein) and one or more exogenous feed enzymes. In one embodiment, the exogenous feed enzymes include, but are not limited to, xylanase, amylase, phytase, beta-glucanase, and protease. In still another embodiment, the composition comprises a feed additive.

1. Xylanases

Xylanase is the name given to a class of enzymes that degrade the linear polysaccharide β-1,4-xylan into xylose, thus breaking down hemicellulose, one of the major components of plant cell walls. Xylanases, e.g., endo-β-xylanases (EC 3.2.1.8) hydrolyze the xylan backbone chain. In one embodiment, provided herein are compositions comprising a multi-strain DFM (such as any of the multi-strain DFM compositions disclosed herein) and one or more xylanase.

In one embodiment, the xylanase may be any commercially available xylanase. Suitably the xylanase may be an endo-1,4-P-d-xylanase (classified as E.G. 3.2.1.8) or a 1,4β-xylosidase (classified as E.G. 3.2.1.37). In one embodiment, the disclosure relates to a DFM in combination with an endoxylanase, e.g. an endo-1,4-P-d-xylanase, and another enzyme. All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3, which is incorporated herein In another embodiment, the xylanase may be a xylanase from *Bacillus, Trichodermna, Therinomyces, Aspergillus* and *Penicillium*. In still another embodiment, the xylanase may be the xylanase in Axtra XAP® or Avizyme 1502®, both commercially available products from Danisco A/S. In one embodiment, the xylanase may be a mixture of two or more xylanases. In still another embodiment, the xylanase is an endo-1,4-β-xylanase or a 1,4-β-xylosidase. In yet another embodiment, the xylanase is from an organism selected from the group consisting of: *Bacillus, Trichoderma, Thermomyces, Aspergillus, Penicillium*, and *Humicola*. In yet another embodiment, the xylanase may be one or more of the xylanases or one or more of the commercial products recited in Table 1.

TABLE 1

Representative commercial xylanases
Representative examples of commercial xylanases.

| Commercial Name ® | Company | Xylanase type | Xylanase source |
|---|---|---|---|
| Allzyme PT | Alltech | endo-1,4-β-xylanase | *Aspergillus Niger* |
| Amylofeed | Andrés Pintaluba S.A | endo-1,4-β-xylanase | *Aspergillus Niger (phoenicis)* |
| Avemix 02 CS | Aveve | endo-1,4-β-xylanase | *Trichoderma reesei* |
| AveMix XG 10 | Aveve, NL | endo-1,4-β-xylanase | *Trichoderma reesei* |
| Avizyme 1100 | Danisco | endo-1,4-β-xylanase | *Trichoderma longibrachiatum* |
| Avizyme 1110 | Danisco | endo-1,4-β-xylanase | *Trichoderma longibrachiatum* |
| Avizyme 1202 | Danisco | endo-1,4-β-xylanase | *Trichoderma longibrachiatum* |
| Avizyme 1210 | Danisco | endo-1,4-β-xylanase | *Trichoderma longibrachiatum* |
| Avizyme 1302 | Danisco | endo-1,4-β-xylanase | *Trichoderma longibrachiatum* |
| Avizyme 1500 | Danisco | endo-1,4-β-xylanase | *Trichoderma longibrachiatum* |
| Avizyme 1505 | Danisco | endo-1,4-β-xylanase | *Trichoderma longibrachiatum* |
| Avizyme SX | Danisco | endo-1,4-β-xylanase | *Trichoderma longibrachiatum* |
| Belfeed MP 100 | Beldem | endo-1,4-β-xylanase | *Bacillus subtilis* |
| Biofeed Plus | DSM | endo-1,4-β-xylanase | *Humicola insolens* |
| Danisco Glycosidase (TPT/L) | Danisco Animal Nutrition | endo-1,4-β-xylanase | *Trichoderma reesei* |
| Danisco Xylanase | Danisco | endo-1,4-β-xylanase | *Trichoderma reesei* |
| Econase XT | AB Vista | endo-1,4-β-xylanase | *Trichoderma reesei* |
| Endofeed ® DC | Andrés Pintaluba S.A. | endo-1,4-β-xylanase | *Aspergillus Niger* |
| Feedlyve AXL | Lyven | endo-1,4-β-xylanase | *Trichoderma longibrachiatum* |
| Grindazym GP | Danisco | endo-1,4-β-xylanase | *Aspergillus Niger* |
| Grindazym GV | Danisco | endo-1,4-β-xylanase | *Aspergillus Niger* |
| Hostazym X | Huvepharma | endo-1,4-β-xylanase | *Trichoderma longibrachiatum* |
| Kemzyme Plus Dry | Kemin | endo-1,4-β-xylanase | *Trichoderma viride* |
| Kemzyme Plus Liquid | Kemin | endo-1,4-β-xylanase | *Trichoderma viride* |
| Kemzyme W dry | Kemin | endo-1,4-β-xylanase | *Trichoderma viride* |
| Kemzyme W liquid | Kemin | endo-1,4-β-xylanase | *Trichoderma viride* |
| Natugrain | BASF | endo-1,4-β-xylanase | *Trichoderma longibrachiatum* |
| Natugrain TS Plus | BASF | endo-1,4-β-xylanase | *Aspergillus Niger* |
| Natugrain Wheat | BASF | endo-1,4-β-xylanase | *Aspergillus Niger* |
| Natugrain ® TS/L | BASF | endo-1,4-β-xylanase | *Aspergillus Niger* |
| Natuzyme | Bioproton | endo-1,4-β-xylanase | *Trichoderma longibrachiatum/ Trichoderma reesei* |
| Porzyme 8100 | Danisco | endo-1,4-β-xylanase | *Trichoderma longibrachiatum* |
| Porzyme 8300 | Danisco | endo-1,4-β-xylanase | *Trichoderma longibrachiatum* |
| Porzyme 9102 | Danisco | endo-1,4-β-xylanase | *Trichoderma longibrachiatum* |
| Porzyme 9310/ Avizyme 1310 | Danisco | endo-1,4-β-xylanase | *Trichoderma longibrachiatum* |
| Porzyme ip 100 | Danisco | endo-1,4-β-xylanase | *Trichoderma longibrachiatum* |
| Ronozyme AX | DSM | endo-1,4-β-xylanase | *Thermomyces lanuginosus* gene expressed in *Aspergillus oryzae* |
| Ronozyme WX | DSM/Novozymes | endo-1,4-β-xylanase | *Thermomyces lanuginosus* gene expressed in *Aspergillus oryzae* |
| Rovabio Excel | Adisseo | endo-1,4-β-xylanase | *Penicillium funiculosum* |

TABLE 1-continued

Representative commercial xylanases
Representative examples of commercial xylanases.

| Commercial Name ® | Company | Xylanase type | Xylanase source |
|---|---|---|---|
| Roxazyme G2 | DSM/Novozymes | endo-1,4-β-xylanase | *Trichoderma longibrachiatum* |
| Safizym X | Le Saffre | endo-1,4-β-xylanase | *Trichoderma longibrachiatum* |
| Xylanase | Lyven | endo-1,4-β-xylanase | *Trichoderma longibrachiatum* |

In one embodiment, the disclosure relates to a composition comprising a multi-strain DFM (such as any of the multi-strain DFM compositions disclosed herein) and xylanase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 xylanase units/g of composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from an oat-spelt-xylan substrate per min at pH 5.3 and 50° C. (Bailey, et al., *Journal of Biotechnology*, Volume 23, (3), May 1992, 257-270).

2. Amylases

Amylase is a class of enzymes capable of hydrolysing starch to shorter-chain oligosaccharides, such as maltose. The glucose moiety can then be more easily transferred from maltose to a monoglyceride or glycosylmonoglyceride than from the original starch molecule. The term amylase includes α-amylases (E.G. 3.2.1.1), G4-forming amylases (E.G. 3.2.1.60), β-amylases (E.G. 3.2.1.2) and γ-amylases (E.C. 3.2.1.3). Amylases may be of bacterial or fungal origin, or chemically modified or protein engineered mutants. In one embodiment, provided herein are compositions comprising a multi-strain DFM (such as any of the multi-strain DFM compositions disclosed herein) and one or more amylase.

In one embodiment, the amylase may be a mixture of two or more amylases. In another embodiment, the amylase may be an amylase, e.g. an α-amylase, from *Bacillus licheniformis* and an amylase, e.g. an α-amylase, from *Bacillus amyloliquefaciens*. In one embodiment, the α-amylase may be the α-amylase in Axtra XAP® or Avizyme 1502®, both commercially available products from Danisco A/S. In yet another embodiment, the amylase may be a pepsin resistant a-amylase, such as a pepsin resistant *Trichoderma* (such as *Trichoderma reesei*) alpha amylase. A suitably pepsin resistant α-amylase is taught in UK application number 101 1513.7 (which is incorporated herein by reference) and PCT/IB2011/053018 (which is incorporated herein by reference).

In one embodiment, the amylase for use in the present invention may be one or more of the amylases in one or more of the commercial products recited in Table 2.

TABLE 2

Representative commercial amylases
Representative examples of commercial amylases.

| Commercial product ® | Company | Amylase type | Amylase source |
|---|---|---|---|
| Amylofeed | Andrés Pintaluba S.A | alpha amylase | *Aspergillus oryzae* |
| Avizyme 1500 | Danisco | alpha amylase | *Bacillus amyloliquefaciens* |
| Avizyme 1505 | Danisco | alpha amylase | *Bacillus amyloliquefaciens* |
| Kemzyme Plus Dry | Kemin | alpha-amylase | *Bacillus amyloliquefaciens* |
| Kemzyme Plus Liquid | Kemin | alpha-amylase | *Bacillus amyloliquefaciens* |
| Kemzyme W dry | Kemin | alpha-amylase | *Bacillus amyloliquefaciens* |
| Kemzyme W liquid | Kemin | alpha-amylase | *Bacillus amyloliquefaciens* |
| Natuzyme | Bioproton | alpha-amylase | *Trichoderma longibrachiatum/Trichoderma reesei* |
| Porzyme 8100 | Danisco | alpha-amylase | *Bacillus amyloliquefaciens* |
| Porzyme ip100 | Danisco | alpha-amylase | *Bacillus amyloliquefaciens* |
| Ronozyme A | DSM/Novozymes | alpha-amylase | *Bacillus amyloliquefaciens* |
| Ronozyme AX | DSM | alpha-amylase | *Bacillus amyloliquefaciens* |
| Ronozyme ® RumiStar (L/CT) | DSM/Novozymes | alpha-amylase | *Bacillus stearothermophilus* expressed in *Bacillus licheniformis* |

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

In one embodiment, disclosure relates to a composition comprising a multi-strain DFM (such as any of the multi-strain DFM compositions disclosed herein) and amylase. In one embodiment, disclosure relates to a composition comprising a multi-strain DFM, xylanase and amylase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-

8500, 8500-9000, 9000-9500, 9500-10000, 10000-11000, 11000-12000, 12000-13000, 13000-14000, 14000-15000 and greater than 15000 amylase units/g composition.

3. Proteases

The term protease as used herein is synonymous with peptidase or proteinase. The protease may be a subtilisin (E.G. 3.4.21.62) or a bacillolysin (E.G. 3.4.24.28) or an alkaline serine protease (E.G. 3.4.21.x) or a keratinase (E.G. 3.4.X.X). In one embodiment, the protease is a subtilisin. Suitable proteases include those of animal, vegetable or microbial origin. Chemically modified or protein engineered mutants are also suitable. The protease may be a serine protease or a metalloprotease. e.g., an alkaline microbial protease or a trypsin-like protease. In one embodiment, provided herein are compositions comprising a multi-strain DFM (such as any of the multi-strain DFM compositions disclosed herein) and one or more protease.

Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In another embodiment, the protease may be one or more of the proteases in one or more of the commercial products recited in Table 3.

In one embodiment, disclosure relates to a composition comprising a multi-strain DFM (such as any of the multi-strain DFM compositions disclosed herein) and a protease. In another embodiment, disclosure relates to a composition comprising a multi-strain DFM (such as any of the multi-strain DFM compositions disclosed herein) and a xylanase and a protease. In still another embodiment, the disclosure relates to a composition comprising a multi-strain DFM (such as any of the multi-strain DFM compositions disclosed herein) and an amylase and a protease. In yet another embodiment, the disclosure relates to a composition comprising a multi-strain DFM (such as any of the multi-strain DFM compositions disclosed herein) and a xylanase, an amylase and a protease.

In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 protease units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

4. Phytases

In one embodiment, provided herein are compositions comprising a multi-strain DFM (such as any of the multi-

TABLE 3

Representative commercial proteases
Representative examples of commercial proteases.

| Commercial product ® | Company | Protease type | Protease source |
|---|---|---|---|
| Avizyme 1100 | Danisco A/S | Subtilisin | *Bacillus subtilis* |
| Avizyme 1202 | Danisco A/S | Subtilisin | *Bacillus subtilis* |
| Avizyme 1302 | Danisco A/S | Subtilisin | *Bacillus subtilis* |
| Avizyme 1500 | Danisco A/S | Subtilisin | *Bacillus subtilis* |
| Avizyme 1505 | Danisco A/S | Subtilisin | *Bacillus subtilis* |
| Kemzyme Plus Dry | Kemin | Bacillolysin | *Bacillus amyloliquefaciens* |
| Kemzyme W dry | Kemin | Bacillolysin | *Bacillus amyloliquefaciens* |
| Natuzyme | Bioproton | Protease | *Trichoderma longibrachiatum/ Trichoderma reesei* |
| Porzyme 8300 | Danisco | Subtilisin | *Bacillus subtilis* |
| Ronozyme ProAct | DSM/Novozymes | Alkaline serine protease | *Nacardiopsis prasina* gene expressed in *Bacillus licheniformis* |
| Versazyme/ Cibenza DP100 | Novus | Keratinase | *Bacillus licheniformis* |

In one embodiment, the protease is selected from the group consisting of subtilisin, a bacillolysin, an alkine serine protease, a keratinase, and a Nocardiopsis protease.

It will be understood that one protease unit (PU) is the amount of enzyme that liberates from the substrate (0.6% casein solution) one microgram of phenolic compound (expressed as tyrosine equivalents) in one minute at pH 7.5 (40 mM $Na_2PO_4$/lactic acid buffer) and 40° C. This may be referred to as the assay for determining 1 PU.

strain DFM compositions disclosed herein) and one or more phytase. The phytase for use in the present invention may be classified a 6-phytase (classified as E.C. 3.1.3.26) or a 3-phytase (classified as E.C. 3.1.3.8). In one embodiment, the phytase for use in the present invention may be one or more of the phytases in one or more of the commercial products below in Table 4:

TABLE 4

Representative commercial phytases

| Commercial product ® | Company | Phytase type | Phytase source |
|---|---|---|---|
| Finase | ABVista | 3-phytase | *Trichoderma reesei* |
| Finase EC | ABVista | 6-phytase | *E. coli* gene expressed in *Trichoderma reesei* |

TABLE 4-continued

Representative commercial phytases

| Commercial product ® | Company | Phytase type | Phytase source |
|---|---|---|---|
| Natuphos | BASF | 3-phytase | *Aspergillus Niger* |
| Natuzyme | Bioproton | phytase (type not specified) | *Trichoderma longibrachiatum/Trichoderma reesei* |
| OPTIPHOS ® | Huvepharma AD | 6-phytase | *E. coli* gene expressed in *Pichia pastoris* |
| Phytase sp1002 | DSM | 3-phytase | A consensus gene expressed in *Hansenula polymorpha* |
| Phyzyme XP | Danisco | 6-phytase | *E. coli* gene expressed in *Schizosaccahomyces pombe* |
| Quantum 2500D, 5000L | ABVista | 6-phytase | *E. coli* gene expressed in *Pichia pastoris* or *Trichoderma* |
| Ronozyme Hi-Phos (M/L) | DSM/Novozymes | 6-phytase | *Citrobacter braakii* gene expressed in *Asperigillus oryzae* |
| Ronozyme NP | DSM/Novozymes | 6-phytase | *Peniphora lycii* gene expressed in *Asperigillus oryzae* |
| Ronozyme P | DSM/Novozymes | 6-phytase | *Peniphora lycii* gene expressed in *Asperigillus oryzae* |
| Rovabio PHY | Adisseo | 3-phytase | *Penicillium funiculosum* |

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter braakii* YH-15 as disclosed in WO 2004/085638, *Citrobacter braakii* ATCC 51113 as disclosed in WO2006/037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius*, *Citrobacter koseri*, *Citrobacter murliniae*, *Citrobacter rodentium*, *Citrobacter sedlakii*, *Citrobacter werkmanii*, *Citrobacter youngae*, *Citrobacter* species polypeptides or variants thereof.

In some embodiments, the phytase is an *E. coli* phytase marketed under the name Phyzyme XP™ Danisco A/S. Alternatively, the phytase may be a *Buttiauxella* phytase, e.g. a *Buttiauxella agrestis* phytase, for example, the phytase enzymes taught in WO 2006/043178, WO 2008/097619, WO2009/129489, WO2008/092901, PCT/US2009/41011 or PCT/IB2010/051804, all of which are incorporated herein by reference.

In one embodiment, the phytase may be a phytase from *Hafnia*, e.g. from *Hafnia alvei*, such as the phytase enzyme(s) taught in US2008263688, which reference is incorporated herein by reference. In one embodiment, the phytase may be a phytase from *Aspergillus*, e.g. from *Apergillus orzyae*. In one embodiment, the phytase may be a phytase from *Penicillium*, e.g. from *Penicillium funiculosum*.

Preferably, the phytase is present in the feedstuff in range of about 200 FTU/kg to about 1000 FTU/kg feed, more preferably about 300 FTU/kg feed to about 750 FTU/kg feed, more preferably about 400 FTU/kg feed to about 500 FTU/kg feed. In one embodiment, the phytase is present in the feedstuff at more than about 200 FTU/kg feed, suitably more than about 300 FTU/kg feed, suitably more than about 400 FTU/kg feed. In one embodiment, the phytase is present in the feedstuff at less than about 1000 FTU/kg feed, suitably less than about 750 FTU/kg feed. Preferably, the phytase is present in the feed additive composition in range of about 40 FTU/g to about 40,000 FTU/g composition, more preferably about 80 FTU/g composition to about 20,000 FTU/g composition, and even more preferably about 100 FTU/g composition to about 10,000 FTU/g composition, and even more preferably about 200 FTU/g composition to about 10,000 FTU/g composition. In one embodiment, the phytase is present in the feed additive composition at more than about 40 FTU/g composition, suitably more than about 60 FTU/g composition, suitably more than about 100 FTU/g composition, suitably more than about 150 FTU/g composition, suitably more than about 200 FTU/g composition. In one embodiment, the phytase is present in the feed additive composition at less than about 40,000 FTU/g composition, suitably less than about 20,000 FTU/g composition, suitably less than about 15,000 FTU/g composition, suitably less than about 10,000 FTU/g composition.

It will be understood that as used herein 1 FTU (phytase unit) is defined as the amount of enzyme required to release 1 µmol of inorganic orthophosphate from a substrate in one minute under the reaction conditions defined in the ISO 2009 phytase assay—A standard assay for determining phytase activity and 1 FTU can be found at International Standard ISO/DIS 30024: 1-17, 2009. In one embodiment, the enzyme is classified using the E.C. classification above, and the E.C. classification designates an enzyme having that activity when tested in the assay taught herein for determining 1 FTU.

C. DFM Formulations

In one embodiment, the DFM (such as any of the multi-strain DFM compositions disclosed herein) and, optionally, exogenous enzymes may be formulated as a liquid, a dry powder or a granule. In one embodiment, the DFMs and exogenous enzymes can be formulated as a single mixture. In another embodiment, the DFMs and the exogenous enzymes can be formulated as separate mixtures. In still another embodiment, separate mixtures of DFMs and the exogenous enzymes can be administered at the same time or at different times. In still another embodiment, separate mixtures of DFMs and the exogenous enzymes can be administered simultaneously or sequentially. In yet another embodiment, a first mixture comprising DFMs can be administered followed by a second mixture comprising exogenous enzymes. In still another embodiment, a first mixture comprising exogenous enzymes can be administered followed by a second mixture comprising DFMs.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

In another embodiment, the DFM and/or the enzyme(s) may be coated, for example encapsulated. Suitably the DFM and enzymes may be formulated within the same coating or encapsulated within the same capsule. Alternatively, one or more of the enzymes may be formulated within the same coating or encapsulated within the same capsule while the DFM can be formulated in a separate coating from the enzymes.

In some embodiments, such as where the DFM is capable of producing endospores, the DFM may be provided without any coating. In such circumstances, the DFM endospores may be simply admixed with one or more enzymes. In the latter case, the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment, all enzymes may be coated, e.g. encapsulated, together. In one embodiment, the coating protects the enzymes from heat and may be considered a thermoprotectant.

In another embodiment, the DFMs and exogenous feed enzymes may be mixed with feed or administered in the drinking water. In one embodiment, the dosage range for inclusion into water is about $1 \times 10^3$ CFU/animal/day to about $1 \times 10^{10}$ CFU/animal/day, for example, about $1 \times 10^7$ CFU/animal/day.

D. Feed Additive Compositions

In one embodiment, provided herein are feed additive compositions comprising one or more DFMs (such as any of the multi-strain DFMs disclosed herein) and, optionally, one or more exogenous feed enzymes. In one embodiment, the feed additive composition can be formulated in any suitable way to ensure that the formulation comprises viable DFMs and, optionally, active enzymes.

In one embodiment, the feed additive composition may be used in the form of solid or liquid preparations or alternatives thereof. Examples of solid preparations include powders, pastes, boluses, capsules, ovules, pills, pellets, tablets, dusts, and granules which may be wettable, spray-dried or freeze-dried. Examples of liquid preparations include, but are not limited to, aqueous, organic or aqueous-organic solutions, suspensions and emulsions.

In another embodiment, the feed additive composition can be used in a solid form. In one embodiment, the solid form is a pelleted form. In solid form, the feed additive composition may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment, the feed additive composition is formulated to a dry powder or granules as described in WO2007/044968 (referred to as TPT granules) or WO 1997/016076 or WO 1992/012645 (each of which is incorporated herein by reference).

In one embodiment, the feed additive composition may be formulated to a granule feed composition comprising: an active agent comprising one or more DFM (such as any of the multi-strain DFM compositions disclosed herein) and, optionally, one or more exogenous feed enzyme and at least one coating. In one embodiment, the active agent of the granule retains activity after processing. In one embodiment, the active agent of the granule retains an activity level after processing selected from the group consisting of: 50-60% activity, 60-70% activity, 70-80% activity, 80-85% activity, 85-90% activity, and 90-95% activity.

In another embodiment, the granule may contain one coating. The coating may comprise a moisture hydrating material that constitutes at least 55% w/w of the granule. In another embodiment, the granule may contain two coatings. The two coatings may be a moisture hydrating coating and a moisture barrier coating. In some embodiments, the moisture hydrating coating may be from 25% to 60% w/w of the granule and the moisture barrier coating may be from 2% to 15% w/w of the granule. The moisture hydrating coating may be selected from inorganic salts, sucrose, starch, and maltodextrin and the moisture barrier coating may be selected from polymers, gums, whey and starch.

In yet another embodiment, the granule may be produced using a feed pelleting process and the feed pretreatment process may be conducted between 70° C. and 95° C. for up to several minutes, such as between 85° C. and 95° C. In another embodiment, the granule may be produced using a steam-heated pelleting process that may be conducted between 85° C. and 95° C. for up to several minutes.

In one embodiment, the granule may have a moisture barrier coating selected from polymers and gums and the moisture hydrating material may be an inorganic salt. The moisture hydrating coating may be between 25% and 45% w/w of the granule and the moisture barrier coating may be between 2% and 20% w/w of the granule.

In one embodiment, the active agent retains activity after conditions selected from one or more of: (a) a feed pelleting process; (b) a steam-heated feed pretreatment process; (c) storage; (d) storage as an ingredient in an unpelleted mixture; and (e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

In some embodiments, the DFM (e.g. DFM endospores, for example) may be diluted using a diluent, such as starch powder, lime stone or the like. In one embodiment, the DFM and the enzymes may be in a liquid formulation suitable for consumption preferably such liquid consumption contains one or more of the following: a buffer, salt, sorbitol and/or glycerol. In another embodiment, the feed additive composition may be formulated by applying, e.g. spraying, the enzyme(s) onto a carrier substrate, such as ground wheat for example.

In one embodiment, the feed additive composition may be formulated as a premix. By way of example only, the premix may comprise one or more feed components, such as one or more minerals and/or one or more vitamins.

In one embodiment, the DFM and exogenous feed enzymes may be formulated with at least one physiologically acceptable carrier selected from at least one of maltodextrin, limestone (calcium carbonate), cyclodextrin, wheat or a wheat component, sucrose, starch, Na2SO4, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In another embodiment, the feed additive composition can be delivered as an aqueous suspension and/or an elixir. The feed additive composition may be combined with various sweetening or flavoring agents, coloring matter or dyes, with emulsifying and/or suspending agents and with diluents such as water, propylene glycol and glycerin, and combinations thereof.

E. Feedstuffs

In another embodiment, provided herein are feed additive compositions containing any of the multi-strain DFM compositions disclosed herein that may be used as a feed or in the preparation of a feed. The feed may be in the form of a solution or as a solid depending on the use and/or the mode of application and/or the mode of administration. When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient.

In one embodiment, the feed additive composition disclosed herein is admixed with a feed component to form a feedstuff. In one embodiment, the feed may be a fodder, or a premix thereof, a compound feed, or a premix thereof. In one embodiment, the feed additive composition disclosed herein may be admixed with a compound feed, a compound feed component or a premix of a compound feed or to a fodder, a fodder component, or a premix of a fodder.

In one embodiment, fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include corn, soybeans, sorghum, oats, and barley.

A "premix," as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; by products from cereals, such as corn gluten meal, Distillers Dried Grain Solubles (DDGS), wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fiber: protein obtained from sources such as sunflower, lupin, fava beans and cotton In still another embodiment, the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment, the feed additive composition of disclosed herein is admixed with the product (e.g. feedstuff). Alternatively, the feed additive composition may be included in the emulsion or raw ingredients of a feedstuff. In another embodiment, the feed additive composition is made available on or to the surface of a product to be affected/treated. In still another embodiment, the feed additive compositions disclosed herein may be applied, interspersed, coated and/or impregnated to a product (e.g. feedstuff or raw ingredients of a feedstuff) with a controlled amount of DFM and, optionally, enzymes.

In yet another embodiment, the DFM and optional enzymes may be used simultaneously (e.g. when they are in admixture together or even when they are delivered by different routes) or sequentially (e.g. they may be delivered by different routes).

In one embodiment, the DFM and optional enzymes are applied to the feedstuff simultaneously. In yet another embodiment, the DFM and optional enzymes are admixed prior to being delivered to a feedstuff or to a raw ingredient of a feedstuff.

In one embodiment, the DFMs in the feed additive compositions disclosed herein can be added in suitable concentrations including but not limited to concentrations in the final feed product that offer a daily dose of from about $2 \times 10^3$ CFU to about $2 \times 10^{11}$ CFU, from about $2 \times 10^6$ to about $1 \times 10^{10}$, and from about $3.75 \times 10^7$ CFU to about $1 \times 10^{10}$ CFU.

III. Methods

A. Methods for Improving Performance Metrics in an Animal

Further provided herein are methods for increasing performance metrics of an animal. In another embodiment, the disclosure relates to methods of increasing performance metrics of a bird. In still another embodiment, the disclosure relates to methods of increasing performance metrics of poultry, including but not limited to broilers, chickens and turkeys.

In yet another embodiment, the disclosure relates to a method comprising administering to an animal a composition comprising DFMs (such as any of the multi-strain DFMs disclosed herein) and, optionally, exogenous feed enzymes. In still another embodiment, the disclosure relates to a method comprising administering to an animal an effective amount of a composition comprising DFMs and optional exogenous feed enzymes to increase performance of the animal. This effective amount can be administered to the animal in one or more doses. In one embodiment, the animal is poultry. In still another embodiment, the animal is a broiler.

In another embodiment, the disclosure relates to a method comprising administering to an animal (such as a domesticated bird, for example, a chicken) an effective amount of a composition comprising DFMs (such as any of the multi-strain DFMs disclosed herein) and optionally exogenous feed enzymes to increase average daily feed intake. In some embodiments, the average daily feed intake increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase average daily weight gain. In some embodiments, the average daily weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase total weight gain. In some embodiments, total weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase feed conversion, which can be measured by either feed:gain or gain:feed. In some embodiments, feed conversion increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase feed efficiency. In some embodiments, feed efficiency increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease mortality. In some embodiments, mortality decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease feed conversion ratio (FCR). In some embodiments, FCR decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase gut barrier integrity. In some embodiments, gut barrier integrity increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. "Gut barrier integrity" can refer to, without limitation, epithelial damage and epithelial permeability which is characterized by a shortening of villi, a lengthening of crypts and an infiltration of inflammatory cells (such as, without limitation, CD3+ cells). The latter damage and inflammation markers can also be associated with a "severe" macroscopic appearance of the gut—compared to a "normal" appearance—when evaluated using a scoring system such as the one described by Teirlynck et al. (2011). In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease or prevent pathogen infection (such as, without limitation, infection by *Clostridium perfringens, Campylobacter jejuni*, a *Salmonela* sp., and/or *Escherichia coli*). In some embodiments, pathogen infection decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease or prevent pathogen shedding in the feces (such as, without limitation, shedding of *Clostridium perfringens, Campylobacter jejuni*, a *Salmonela* sp., and/or *Escherichia coli*). In some embodiments, pathogen shedding in the feces decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In still another embodiment, the DFM composition (such as a feed or feed additive composition) administered to the animal (such as a domesticated bird, for example, a chicken) is a multi-strain DFM comprising one or more of *A. colihominis* strain W1 (CBS 146120), or a strain having all of the identifying characteristics of *A. colihominis* strain W1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W1 (SEQ ID NO:1); *Anaerotruncus colihominis* strain W2 (CBS 146122), or a strain having all of the identifying characteristics of *A. colihominis* strain W2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W2 (SEQ ID NO:2); *Anaerotruncus colihominis* strain W3 (CBS 146123), or a strain having all of the identifying characteristics of *A. colihominis* strain W3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W3 (SEQ ID NO:3); and/or *Anaerotruncus colihominis* strain W4 (CBS 146121), or a strain having all of the identifying characteristics of *A. colihominis* strain W4, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W4 (SEQ ID NO:4). In another embodiment, the DFM composition includes *A. colihominis* strains W1 and W2; *A. colihominis* strains W1 and W3; *A. colihominis* strains W1 and W4; *A. colihominis* strains W2 and W3; *A. colihominis* strains W2 and W4; *A. colihominis* strains W3 and W4; *A. colihominis* strains W1, W2, and W3; *A. colihominis* strains W1, W3, and W4; *A. colihominis* strains W2, W3, and W4; or *A. colihominis* strains W1, W2, W3, and W4. In some embodiments, the one or more *A. colihominis* strain(s) is (are) administered to an animal at a rate of at least $1 \times 10^4$ CFU/animal/day. For poultry, according to one non-limiting embodiment, the one or more *A. colihominis* strain(s) can be fed at about $1 \times 10^5$ CFU/g feed to about $1 \times 10^{10}$ CFU/g feed. In at least some embodiments, the one or more *A. colihominis* strains is (are) fed at about $1 \times 10^5$ CFU/bird/day or about $1 \times 10^8$ CFU/bird/day.

In still another embodiment, the DFM composition (such as a feed or feed additive composition) administered to the animal (such as a domesticated bird, for example, a chicken) is a multi-strain DFM comprising one or more of *Coprococcus* sp. strain M1 (CBS 146125), or a strain having all of the identifying characteristics *Coprococcus* sp. strain M1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *Coprococcus* sp. strain M1 (SEQ ID NO:5); *A. colihominis* strain M2 (CBS 146119), or a strain having all of the identifying characteristics of *A. colihominis* strain M2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain M2 (SEQ ID NO:6); *C. lactatifermentans* strain M3 (CBS 146124), or a strain having all of the identifying characteristics of *C. lactatifermentans* strain M3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *C. lactatifermentans* strain M3 (SEQ ID NO:7); and/or a *P. capillosus* strain (such as *P. capillosus* strain M4) or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *P. capillosus* strain M4 (SEQ ID NO:8). In some embodiments, the DFM composition includes only *Coprococcus* sp. strain M1, *A. colihominis* strain M2, *C. lactatifermentans* strain M3, or a *P. capillosus* strain (such as *P. capillosus* strain M4). In another embodiment, the DFM composition includes *Coprococcus* sp. strain M1 and *A. colihominis* strain M2; *Coprococcus* sp. strain M1 and *C. lactatifermentans* strain M3; *Coprococcus* sp. strain M1 and a *P. capillosus* strain (such as *P. capillosus* strain M4); *A. colihominis* strains M2 and *C. lactatifermentans* strain M3; *A. colihominis* strain M2 and a *P. capillosus* strain (such as

*P. capillosus* strain M4); *C. lactatifermentans* strain M3 and a *P. capillosus* strain (such as *P. capillosus* strain M4); *Coprococcus* sp. M1, *A. colihominis* strain M2, and *C. lactatifermentans* strain M3; *Coprococcus* sp. strain M1, *C. lactatifermentans* strain M3, and a *P. capillosus* strain (such as *P. capillosus* strain M4); *A. colihominis* strain M2, *C. lactatifermentans* strain M3, and *P. capillosus* strain M4; or *Coprococcus* sp. strain M1, *A. colihominis* strain M2, *C. lactatifermentans* strain M3, and a *P. capillosus* strain (such as *P. capillosus* strain M4). In some embodiments, the one or more M1, M2, M3, and/or M4 strain(s) is (are) administered to an animal at a rate of at least $1\times10^4$ CFU/animal/day. For poultry, according to one non-limiting embodiment, the one or more M1, M2, M3, and/or M4 strain(s) can be fed at about $1\times10^5$ CFU/g feed to about $1\times10^{10}$ CFU/g feed. In at least some embodiments, the one or more M1, M2, M3, and/or M4 strains is (are) fed at about $1\times10^5$ CFU/bird/day or about $1\times10^8$ CFU/bird/day.

In still another embodiment, the DFM composition (such as a feed or feed additive composition) administered to the animal (such as a domesticated bird, for example, a chicken) is a multi-strain DFM comprising one or more of *C. lactatifermentans* strain 2F1 (CBS 146124), or a strain having all of the identifying characteristics *C. lactatifermentans* strain 2F1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *C. lactatifermentans* strain 2F1 (SEQ ID NO:9); *L. salivarius* strain 2F2 (CBS 146126), or a strain having all of the identifying characteristics of *L. salivarius* strain 2F2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain 2F2 (SEQ ID NO:10); and/or *L. reuteri* strain 2F3 (CBS 145921), or a strain having all of the identifying characteristics of *L. reuteri* strain 2F3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain 2F3 (SEQ ID NO:11). In some embodiments, *L. reuteri* strain 2F3 produces reuterin (3-hydroxypropionaldehyde). In other embodiments, *L. reuteri* strain 2F3 does not produce reuterin (3-hydroxypropionaldehyde). In some embodiments, the DFM composition includes only *C. lactatifermentans* strain 2F1, *L. salivarius* strain 2F2, or *L. reuteri* strain 2F3. In another embodiment, the DFM composition includes *C. lactatifermentans* strain 2F1 and *L. salivarius* strain 2F2; *C. lactatifermentans* strain 2F1 and *L. reuteri* strain 2F3; *L. salivarius* strain 2F2 and *L. reuteri* strain 2F3; or *C. lactatifermentans* strain 2F1, *L. salivarius* strain 2F2, and *L. reuteri* strain 2F3. In some embodiments, the one or more 2F1, 2F2 and/or 2F3 strain(s) is (are) administered to an animal at a rate of at least $1\times10^4$ CFU/animal/day. For poultry, according to one non-limiting embodiment, the one or more 2F1, 2F2 and/or 2F3 strain(s) can be fed at about $1\times10^5$ CFU/g feed to about $1\times10^{10}$ CFU/g feed. In at least some embodiments, the one or more 2F1, 2F2 and/or 2F3 strains is (are) fed at about $1\times10^5$ CFU/bird/day or about $1\times10^8$ CFU/bird/day.

The DFM compositions provided herein can be administered, for example, as a strain-containing culture solution, a strain-containing supernatant, or a bacterial product of a culture solution. Administration of a composition comprising a DFM and optional exogenous feed enzymes provided herein to an animal can increase the performance of the animal. In one embodiment, administration of a DFM provided herein to an animal can increase the average daily feed intake (ADFI), average daily gain (ADG), or feed efficiency (gain:feed; G:F) (collectively, "performance metrics"). One or more than one of these performance metrics may be improved.

The composition comprising DFMs and exogenous feed enzymes may be administered to the animal in one of many ways. For example, the composition can be administered in a solid form as a veterinary pharmaceutical, may be distributed in an excipient, preferably water, and directly fed to the animal, may be physically mixed with feed material in a dry form, or the composition may be formed into a solution and thereafter sprayed onto feed material. The method of administration of the compositions disclosed herein to the animal is considered to be within the skill of the artisan.

When used in combination with a feed material, the feed material can include corn, soybean meal, byproducts like distillers dried grains with solubles (DDGS), and vitamin/mineral supplement. Other feed materials can also be used.

Thus, in at least some embodiments, the effective amount of the composition comprising DFMs and optional exogenous feed enzymes is administered to an animal by supplementing a feed intended for the animal. As used herein, "supplementing," refers to the action of incorporating the effective amount of bacteria provided herein directly into the feed intended for the animal. Thus, the animal, when feeding, ingests the bacteria provided herein.

B. Methods for Preparing a Feed Additive Composition

Also provided herein are methods for preparing a feed additive composition comprising combining two or more of the DFMs disclosed herein. In some embodiments, the method includes combining two or more (such as any of 2, 3, or 4) of *A. colihominis* strain W1 (CBS 146120), or a strain having all of the identifying characteristics of *A. colihominis* strain W1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W1 (SEQ ID NO:1); *Anaerotruncus colihominis* strain W2 (CBS 146122), or a strain having all of the identifying characteristics of *A. colihominis* strain W2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W2 (SEQ ID NO:2); *Anaerotruncus colihominis* strain W3 (CBS 146123), or a strain having all of the identifying characteristics of *A. colihominis* strain W3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W3 (SEQ ID NO:3); and/or *Anaerotruncus colihominis* strain W4 (CBS 146121), or a strain having all of the identifying characteristics of *A. colihominis* strain W4, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain W4 (SEQ ID NO:4). In another embodiment, *A. colihominis* strains W1 and W2 are combined; *A. colihominis* strains W1 and W3 are combined; *A. colihominis* strains W1 and W4 are combined; *A. colihominis* strains W2 and W3 are combined; *A. colihominis* strains W2 and W4 are combined; *A. colihominis* strains W3 and W4 are combined; *A. colihominis* strains W1, W2, and W3 are combined; *A. colihominis* strains W1, W3, and W4 are combined; *A. colihominis* strains W2, W3, and W4 are combined; or *A. colihominis* strains W1, W2, W3, and W4 are combined.

In yet further embodiments, the method includes combining two or more (such as any of 2, 3, or 4) of *Coprococcus* sp. strain M1 (CBS 146125), or a strain having all of the identifying characteristics *Coprococcus* sp. strain M1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *Coprococcus* sp. strain M1 (SEQ ID NO:5); *A. colihominis* strain M2 (CBS 146119), or a strain having all of the identifying characteristics of *A. colihominis* strain M2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *A. colihominis* strain M2 (SEQ ID NO:6); *C. lactatifermentans* strain M3 (CBS 146124), or a strain having all of the identifying characteristics of *C. lactatifermentans* strain M3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *C. lactatifermentans* strain M3 (SEQ ID NO:7); and/or a strain having all of the identifying characteristics of a *P. capillosus* strain (such as *P. capillosus* strain M4) or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *P. capillosus* strain M4 (SEQ ID NO:8). In another embodiment, *Coprococcus* sp. strain M1 and *A. colihominis* strain M2 are combined; *Coprococcus* sp. strain M1 and *C. lactatifermentans* strain M3 are combined; *Coprococcus* sp. strain M1 and *P. capillosus* strain M4 are combined; *A. colihominis* strains M2 and *C. lactatifermentans* strain M3 are combined; *A. colihominis* strain M2 and *P. capillosus* strain M4 are combined; *C. lactatifermentans* strain M3 and *P. capillosus* strain M4 are combined; *Coprococcus* sp. strain M1, *A. colihominis* strain M2, and *C. lactatifermentans* strain M3 are combined; *Coprococcus* sp. strain M1, *C. lactatifermentans* strain M3, and *P. capillosus* strain M4 are combined; *A. colihominis* strain M2, *C. lactatifermentans* strain M3, and *P. capillosus* strain M4 are combined; or *Coprococcus* sp. strain M1, *A. colihominis* strain M2, *C. lactatifermentans* strain M3, and *P. capillosus* strain M4 are combined.

In additional embodiments, the method includes combining two or more (such as any of 2 or 3) of *C. lactatifermentans* strain 2F1 (CBS 146124), or a strain having all of the identifying characteristics *C. lactatifermentans* strain 2F1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *C. lactatifermentans* strain 2F1 (SEQ ID NO:9); *L. salivarius* strain 2F2 (CBS 146126), or a strain having all of the identifying characteristics of *L. salivarius* strain 2F2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain 2F2 (SEQ ID NO:10); and/or *L. reuteri* strain 2F3 (CBS 145921), or a strain having all of the identifying characteristics of *L. reuteri* strain 2F3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain 2F3 (SEQ ID NO:11). In another embodiment, *C. lactatifermentans* strain 2F1 and *L. salivarius* strain 2F2 are combined; *C. lactatifermentans* strain 2F1 and *L. reuteri* strain 2F3 are combined; *L. salivarius* strain 2F2 and *L. reuteri* strain 2F3 are combined; or *C. lactatifermentans* strain 2F1, *L. salivarius* strain 2F2, and *L. reuteri* strain 2F3 are combined.

Additionally, the methods for preparing a feed additive composition can further include combining the feed additive composition with one or more of the exogenous enzymes disclosed herein (for example, one or more of a phytase, a protease, an amylase, a xylanase or a beta-glucanase). The method can additionally include a further step of packaging the feed additive composition for storage or transport.

IV. Kits

Further provided herein are kits containing one or more of the DFMs (such as one or more of the multi-strain DFMs) disclosed herein. The kits can include one or more of (such as any of 1, 2, 3, 4, 5, 6, 7, 8, 9, 10, or 11) the strains provided herein inlcuding *Anaerotruncus colihominis* strain W1 (CBS 146120), *Anaerotruncus colihominis* strain W2 (CBS 146122), *Anaerotruncus colihominis* strain W3 (CBS 146123), *Anaerotruncus colihominis* strain W4 (CBS 146121), *Coprococcus* sp. strain M1 (CBS 146125), *Anaerotruncus colihominis* strain M2 (CBS 146119), *Clostridium lactatifermentans* strain M3 (CBS 146124), a *Pseudoflavonifractor capillosus* strain (such as *P. capillosus* strain M4), *Clostridium lactatifermentans* strain 2F1 (CBS 146124), *Lactobacillus salivarius* strain 2F2 (CBS 146126), and *Lactobacillus reuteri* strain 2F3(CBS 145921) along with instructions for proper storage, maintenance, and use for administering to an animal to improve one or more performance metrics. In one embodiment, the kit can include strains W1, W2, W3, and/or W4. In another embodiment, the kit can include strains M1, M2, M3, and/or M4. In a further embodiment, the kit can include strains 2F1, 2F2, and/or 2F3. The kits can additionally include one or more of the exogenous enzymes disclosed herein (for example, one or more of a phytase, a protease, an amylase, a xylanase or a beta-glucanase).

The invention can be further understood by reference to the following examples, which are provided by way of illustration and are not meant to be limiting.

EXAMPLES

Example 1: Methods and Assays

In the following examples, various methods and assays were used as set forth below for ease in reading. Any deviations from the protocols provided below are indicated in the relevant sections.

Isolation of anaerobic microbes from chicken intestinal tracts: To isolate strict anaerobes, GIT samples dissected in the field were transferred into anaerobic transport media as quickly as possible. Strain isolation started once intestinal samples arrived at the lab. Ceca, ileum, jejunum or duodenum samples were dissected using sterile technique inside an anaerobic chamber. The digesta was discarded and mucosal-bound material was scraped using a loop. This material was then transferred into sterile media or buffer and serially diluted. Serial dilutions ranging from $10^{-1}$ to $10^{-6}$ were plated onto petri dishes or omni plates of various media types using plating beads. These plates were then incubated anaerobically until colonies became visible. For obligate anaerobes, brain heart infusion medium (BHI) was used.

Once colonies were visible on an agar plate, colonies were picked in the anaerobic chamber to liquid media in a 96 deep well plate. Some plates were initially picked into a small volume of liquid media (i.e. 200 µl) and then media added to 800 µl 1-4 days later to increase growth. Colony picking could be done at multiple time points for the same plate. For example, large colonies were picked on day 2, and then very small colonies or new colonies were picked at day 5.

Sample preparation and analysis of short-chain fatty acid production: Supernatants of bacterial cultures were evaluated for short-chain fatty acid (SCFA) production by GC methods. Cell cultures were centrifuged at 4° C. at 4100 RPM and 300 µl of the supernatant was removed by filtering through 0.2 um filter multi-well plate filtering unit (Pall Corporation, Product ID 8119). 150 µl of filtered supernatant was added to 150 µl of 0.5% $H_3PO_4$ solution, and filtered again through 0.2 µm filter plate. 140 µl of the prepared supernatant sample was transferred to a GC vial with volume inserts for GC-FID analysis.

GC separation of SCFAs on FFAP column has been previously reported (Zhao et al 2005). The GC instrumental method was modified to reduce sample run time to approximately 8 minutes. SCFA chromatographic analysis was carried out using Agilent 7890A GC system equipped with FID detector. A fused silica capillary column with a free-fatty acid phase was used (Agilent P/N 122-3232 DB-FFAP, 30 m×0.25 mm diameter, 0.25 µm film thickness). Helium gas was used as the carrier gas. The GC instrumental method was optimized to increase analysis time. The inlet temperature was 250° C. with 22.192 psi inlet pressure. The method was run under constant flow of 1.8 mL/min carrier gas flow rate. The initial oven temperature was 100° C., maintained for 0.3 min, raised to 240° C. at 17.5° C./min, with no hold time at final 240° C. temperature. The average gas velocity with these parameters was >42 cm/sec. The temperature of the FID was 300° C. The instrumental parameters reduced runtime to approximately 8 minutes. GC grade standards were used for external calibration.

Analysis of the microbial composition of mucosa region of the small intestines by 16S sequencing and netB qPCR: To evaluate the microbial composition of the small intestines, chicken swabs of the mucosa region of the small intestines was analyzed by 16S sequencing. Chicken gastro intestinal tract (GIT) is removed and separated into four sections: duodenum, jejunum, ileum and ceca. Each section is squeezed to remove the digesta contents and then cut longitudinally to expose the inner surface. Each section inner surface is swabbed with a FLOQSwab (Copan Mfgr, Murrieta, CA). The swab is added directly to a well of a 96 well Qiagen MagAttract PowerSoil kit (Qiagen, Hilden, Germany). The swabs were processed for bacterial DNA isolation as per the manufacturer's instructions using the KingFisher Flex automation platform. Isolated metagenomic DNA is then ready for NGS sample preparation Metagenomic DNA purified from chicken GIT swabs was prepared for 16S community sequencing as follows: DNA is diluted 1:5 by adding 20 µl of molecular biology grade water to 5 µl of purified DNA at 0.1-10 ng/µl. Then 2 µl of the diluted DNA was added to a PCR reaction along with 25 ul of ABI Universal TaqMan Reaction mix without UNG (ThermoFisher #4326614), 0.1 µl each PCR primers at 100 uM and 24.8 µl of Molecular Biology Grade water for a total volume of 50 ul. The PCR primers were the Illumina-V4-515F-RJ: TCGTCGGCAGCGTCAGATGTGTATAAGA-GACAGGTGCCAGCMGCCGCGGTAA and Illumina-V4-806R-RJ: GTCTCGTGGGCTCGGAGATGTGTATAAGA-GACAGGGACTACHVGGGTWTCTAAT were used. The PCR reactions were: 10 min at 95° C. followed by 35 cycles of 95° C. 15 sec+55° C. 30 sec+72° C. for 2 min. Amplified reactions were purified using Ampure XP Magnetic Beads (Beckman Coulter A63881) as per manufacturer's instructions using the Agilent Bravo Automated Robotic Workstation. 2 µl of each amplicon pool was then indexed in a second PCR reaction using the same conditions as above with Illumina XT Index Primers (Illumina XT v2.0 #FC-131-2001-2004) for 15 cycles. Indexed amplicons are then pooled and purified with AmPure XP Magnetic Beads on the Agilent Bravo Automated Robotic Workstation. Pooled, indexed amplicons were quantitated using the Kapa Illumina Library Quantification Kit (KAPA #KK4835) as per manufacturer's instructions. Purified, quantitated, indexed, pools were loaded on the Illumina MiSeq at a final concentration of 8 pM along with 15% Illumina PhiX (Illumina FC-110-3001). Sequencing was run for 2×250 Paired End cycles.

The 16S Amplicon data from Illumina Miseq sequencing were analyzed. Paired-end reads were first merged by Flash (Mogoc et al., *Bioinformatics*. 2011; 27:2957-63). The forward and reverse primers were removed from the merged reads, and reads with overall quality score less than 20 were discarded by RDP Initial Process tool (Fish et al., *Front Microbiol.* 2013; 4:291). This step also removes reads originated from chicken mitochondria due to their length shorter than 200 bp. In the next step reads were assigned to bacterial and archaeal taxonomy by RDP Classifier (Wang et al., *Appl Environ Microbiol.* 73(16):5261-5267). The reads passed the above quality processing steps were clustered at 98% by CD-HIT (Li & Godzik, *Bioinformatics,* 2006; 22:1658-9) to obtain Operational Taxonomic Units (OTU). The representative sequence from each OTU was assigned to the closest species by RDP pairwise alignment tool (Fish et al., *Front Microbiol.* 2013; 4:291) against a vetted 16S reference database containing mostly 16S genes from type strains and public genomes. The relative abundance of an OTU in a sample was the fraction of reads assigned to that OTU. An OTU was assigned to a species if it has at least 98% identity to that species in the reference database. The average abundance of a species in a consortium in small intestine was calculated as the average relative abundance of that species from DUO, JEJ and ILL samples of each treatment.

The same DNA preparations were also quantified for netB gene using qPCR. NetB is an important virulence factor for *C. perfringens*. Each assay was run using 1.5 µl of DNA along with 10 µl of TaqMan Universal Master Mix, 0.2 µl of 100 uM Forward and Reverse Primers, 0.05 µl of TaqMan Probe, and 9.55 µl Molecular Biology Grade water. The qPCR reaction conditions were as follows: 10 min at 95° C.+40 cycles of 95° C. 15 sec+60° C. 60 sec on the ABI Quant Studio qPCR instrument. Sample data was quantified using genomic DNA from a netB positive *C. perfringens*. Primer and probe sequences used are in Table 5 below:

TABLE 5 qPCR Primers and Probes

| Target | Primer Name | Direction | Sequence (5' to 3') |
|---|---|---|---|
| Total Bacteria 16S | 16S-T1-1369F | for | CGGTGAATACGTT CYCGG |
|  | 16S-T1-1492R | rev | GGWTACCTTGTTA CGACTT |
|  | 16S-T1-1389T | probe | CTTGTACACACCG CCCGTC |
| C. perfringens | CPerf165F | for | CGCATAACGTTGA AAGATGG |
|  | CPerf269R | rev | CCTTGGTAGGCCG TTACCC |
|  | CPerf187T | probe | TCATCATTCAACC AAAGGAGCAATCC |
| netB gene | NetB-RJ-Fwd | Fwd | TGGTGCTGGAATA AATGCTTCAT |
|  | NetB-RJ-Rev | Rev | TGCATCATCTTTT CTTTGAATTGTTC |
|  | NetB-RJ-MGB | Probe | ATACTATAAGCTA TGAACAACC |

Figure 1B:
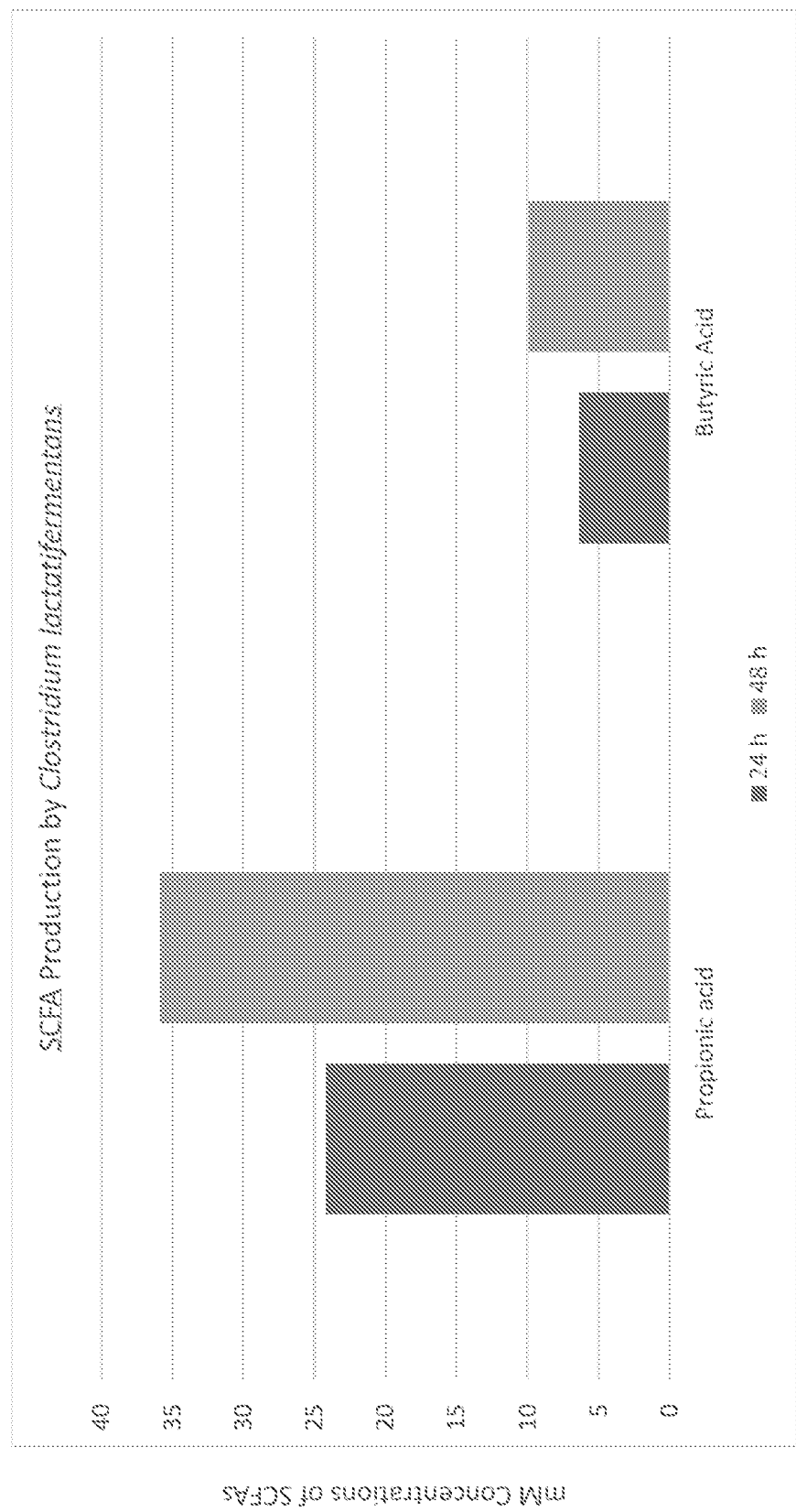
FIG. 1B depicts a bar graph showing SCFA production by *Clostridium lactatifermentans* in culture at 24 and 48 hours.

Example 2: Short-Chain Fatty Acid Production by Obligate Anaerobic Bacteria from Broiler Chicken Based on the method described in Example 1, a variety of obligate anaerobes were identified which produce SCFAs, including both Gram-positive and Gram-negative bacteria. Table 6 lists the production of butyrate and propionate from non-limiting examples of bacteria isolated from chicken intestinal tracts. Most of them produced butyrate as the major SCFA (FIG. 1A). One strain, *Clostridium lactatifermentans* M3, on the other hand, produced propionate as the major SCFA (FIG. 1B).

TABLE 6

Short-chain fatty acid production (mM) by certain obligate anaerobes

| Strains | Butyrate | Propionate |
|---|---|---|
| *Clostridium* MSTE9 2A1 | 7.68 | ND |
| *Clostridium* MSTE9 2A2 | 12.04 | ND |
| *Clostridium* MSTE9 2A3 | 6.14 |  |
| *Clostridium nexile* Z1 | 10.76 | ND |
| *Clostridium nexile* Z2 | 16.21 | ND |
| *Clostridium nexile* Z3 | 8.95 | ND |
| *Clostridium nexile* Z4 | 16.31 | ND |

TABLE 6-continued

Short-chain fatty acid production (mM) by certain obligate anaerobes

| Strains | Butyrate | Propionate |
|---|---|---|
| *Coprococcus* sp. M1 | 25.37 | ND |
| *Anaerotruncus colihominis* M2 | 25.37 | ND |
| *Clostridium lactatifermentans* M3 | 9.22 | 54.63 |
| *Pseudoflavonifractor capillosus* M4 | 22.00 | ND |
| *Anaerotruncus colihominis* W1 | 17.3 | ND |
| *Anaerotruncus colihominis* M2 | 15.67 | ND |
| *Anaerotruncus colihominis* M3 | 21.01 | ND |
| *Anaerotruncus colihominis* M4 | 8.00 | ND |

Figure 2:
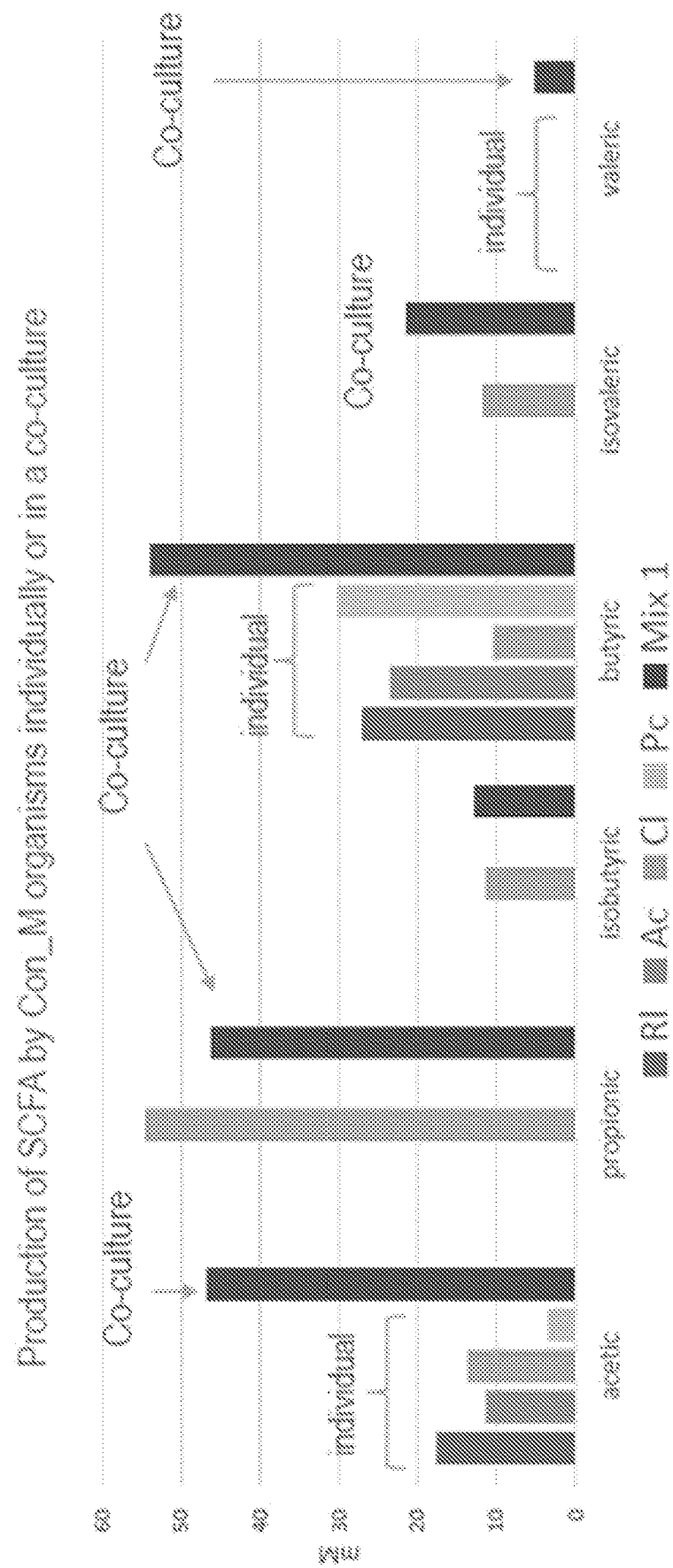
FIG. 2 depicts a bar graph showing SCFA production by bacteria individually as well as in co-culture. R1=*Coprococcus* sp. strain M1; Ac=*Anaerotruncus colihominis* strain M2; Cl=*Clostridium lactatifermentans* strain M3; and Pc=*Pseudoflavonifractor capillosus* strain M4.

To evaluate the potential interaction of SCFA producing microbes, four SCFA producing microbes were mixed as c-culture in the BHI medium. These four organisms were *Coprococcus* sp. M1, *Anaerotruncus colihominis* M2, *Clostridium lactatifermentans* M3, and *Pseudoflavonifractor capillosus* M4 as listed in Table 6. The SCFA contents were analyzed in the supernatant. As shown in Table 7, the amount of propionate from the co-culture was proportional to the amount generated by *Clostridium lactatifermentans* as measured in the individual culture. However, the amount of butyrate production in the co-culture was higher than the amount generated by any individual strain, suggesting an additive effect. For the valerate production, it was not detected in any of the individual strain cultured alone. The co-culture, on the other hand, produced valerate, suggesting synergistic effect (FIG. 2). Valerate has been demonstrated to have efficacy for reducing the incidence of necrotic enteritis (*Poult Sci.* 2018 Jul. 1; 97(7):2303-2311).

TABLE 7

Comparison of SCFA profiles by individual culture and mixed culture.

| Strains | Butyrate | Propionate | Acetate | Valerate |
|---|---|---|---|---|
| *Coprococcus* sp. M1 | 25.37 | ND | 16.69 | ND |
| *Anaerotruncus colihominis* M2 | 25.37 | ND | 10.59 | ND |
| *Clostridium lactatifermentans* M3 | 9.22 | 54.63 | 11.11 | ND |
| *Pseudoflavonifractor capillosus* M4 | 22 | ND | 5.53 | ND |
| Mixture of above 4 strains | 51.52 | 42.75 | 45.27 | 5.01 |

Example 3: Evaluation of SCFA Producing Bacteria for the Prevention of Necrotic Enteritis Through Aanimal Studies A challenged diseased model for broiler chicken has been used extensively (*Front Microbiol.* 2016, 7:1416; *J Anim Sci Biotechnol.* 2018, 9:25; *Poult Sci.* 2018, Nov. 18). In this experiment, chickens at day 9 were first challenged with live 1× Eimeria vaccine (ADVENT® coccidiosis vaccine, Huvepharma, Inc., Lincoln, NE 68528). Seventeen (17) birds were in each of the experimental and control groups. The vaccine was diluted in water and each chicken received 1 ml orally. At day 11, each chicken received 1 ml of pathogen cocktail orally. The pathogen cocktail consisted of five *Clostridium perfringens* strains isolated from diseased tissues. All strains contained the netB and Tpel genes based on the genome analysis. These strains were grown individually in cooked meat medium (Sigma) overnight and the fresh cultures were mixed in equal volume in a glove box to make up the cocktail. The cocktail was used the same day to induce necrotic enteritis.

With this disease model, DFM candidates were evaluated for their efficacy against *C. perfringens* infection. For anaerobic bacteria DFM candidates were grown in BHI medium under anaerobic conditions. and the fresh culture were mixed in equal volume inside the glovebox to make up a specific consortium for the animal trial. The mixed cell suspension for each consortium was aliquoted into serum bottles under anaerobic conditions inside a glove box. The serum bottles were stored at 80° C. and thawed before use. The DFM consortia were fed to each chicken daily by gavage starting at day 1. At day 15, chicken intestines were collected for histopathology analysis and the mucosa samples were used for DNA isolation as described in Example 1.

The DFM consortia and their strain composition are listed in Table 8. For the first animal trial, consortia K, and N consisted of anaerobic microbes that do not produce SCFAs. Only consortium M consisted of strains that can produce SCFAs. For the control group of chicken, no DFM candidates were used. For the second animal trial, all consortia consisted microbes that can produce SCFAs.

TABLE 8

List of consortia and their strain compositions used for animal trials

| Consortia | Components |
|---|---|
| | Trial 1 |
| K | *Clostridium glycyrrhizinilyticum* K1, *Anaerofilum agile* K2, *Bacteroides dorei* K3 |
| M | *Coprococcus* sp. M1, *Anaerotruncus colihominis* M2, *Clostridium lactatifermentans* M3, *Pseudoflavonifractor capillosus* M4 |
| N | *Bacteroides cellulosilyticus* N1, *Bacteroides fragilis* N2, *Parabacteroides distasatonis* N3 |
| | Trial 2 |
| 2A | *Clostridium* sp. MSTE9 2A1, *Clostridium* sp. MSTE9 2A2, *Clostridium* sp. MSTE9 2A3 |
| Z | *Clostridium* sp. MSTE9 2A1, *Clostridium* sp. MSTE9 2K2, *Clostridium* sp. MSTE9 2A3 |
| W | *Anaerotruncus colihominis* W1, *Anaerotruncus colihominis* M2, *Anaerotruncus colihominis* M3, *Anaerotruncus colihominis* M4 |

The abundance of *C. perfringens* based on 16S analysis using samples from day 15 as described in Example 1 is summarized in Table 9. Consortia K and N included different anaerobic bacteria (Table 8). These microbes did not produce SCFAs. Based on 16S analysis, chicken feed with these two consortia showed similar abundance of *C. perfringens* as the chicken in the disease model group. The result from qPCR analysis of the netB gene showed a similar trend. This suggests that these two DFM consortia did not show efficacy against the expansion of the pathogen in the animal trial. Consistent with this observation, histopathology analysis showed the presence of necrotic enteritis in these samples. On the other hand, the abundance of *C. perfringens* was much lower in consortium M. This consortium consisted of four different anaerobic strains that produced SCFAs as described in Example 2. Interestingly, as demonstrated in Example 2, when these four strains were mixed as co-culture, the SCFAs profile was different in comparison to when these strains are cultured individually. Histopathology indicated no sign of necrotic enteritis. This suggests that consortium M had efficacy in the prevention of *C. perfringens* infection.

To further investigate whether other SCFA producing microbes isolated from chicken would have similar effect on reducing the incidence of necrotic enteritis, consortia 2A, Z, and W were designed and used in another animal trial (Table 8; Trial 2). Based on 16S analysis and netB qPCR (Table 9), consortia, 2A and Z, showed high abundance of *C. perfringens* in the small intestines. Histopathology analysis indicated necrotic enteritis just like the disease model. This result suggests that these two SCFA-producing consortia had no impact. On the other hand, a new consortium, W, was found to be efficacious against the pathogen. This consortium consisted of isolates from the *Anaerotruncus colihominis* species.

TABLE 9

Results of animal trials

| Consortium | CP Abundance[1] | netB qPCR[2] | Necrotic Enteritis |
|---|---|---|---|
| | Trial 1 | | |
| Model | 0.173 | 0.204 | Positive |
| K | 0.507 | 0.828 | Positive |
| M | 0.004 | 0.001 | Negative |
| N | 0.281 | 0.314 | Positive |

TABLE 9-continued

Results of animal trials

| Consortium | CP Abundance[1] | netB qPCR[2] | Necrotic Enteritis |
|---|---|---|---|
| | Trial 2 | | |
| Model | 0.197 | 0.195 | Positive |
| 2A | 0.785 | 1.447 | Positive |
| Z | 0.688 | 1.749 | Positive |
| W | 0.002 | 0.04 | Negative |

[1]CP Abundance = 16S CP sequence reads/Total 16S Sequence reads (Example 1)

[2]netB qPCR = qPCR netB Copy number/qPCR Total 16S

Example 4: A Combination SCFA Producing Microbe with *Lactobacillus* Species

To investigate a combination of a SCFA producing microbe with other potential DFM candidates that do not produce SCFAs, another animal trial was carried out with consortium 2F (Table 10). Consortium 2F consisted of *C. Lactatifermentans* M3, a SCFA producer from consortium M (Table 6), and two different isolates of *Lactobacillus*.

TABLE 10

Combined SCFA producer and *Lactobacillus* consortium and strain composition used for trial

| Consortia | Components |
|---|---|
| | Trial 3 |
| 2F | *C. Lactatifermentans* M3, *L. salivarius* U1, *L. reuteri* S1 |

As shown in Table 11, feeding consortium to the animal greatly reduced the CP counts based on both 16S analysis and netB PCR quantification as compared to the model where no DFM candidates were used. In addition, no necrotic enteritis was detected in the small intestines of chicken treated with 2F consortium. The result indicated that a combination of a SCFA producer and *Lactobacillus* species as present in the 2F consortium had the efficacy of preventing the CP infection.

TABLE 11

Results of animal trials

| Consortium | CP Abundance[1] | netB qPCR[2] | Necrotic Enteritis |
|---|---|---|---|
| | | Trial 3 | |
| Model | 0.427 | 0.466 | Positive |
| 2F | 0.001 | 0.066 | Negative |

SEQUENCES
A. colihominis strain W1 16S rRNA (SEQ ID NO: 1)

CAAAGGAGCAATCCGCTGAAAGATGGGCTCGCGTCCGATTAGCCAGTTGGCGGGGTAACGG

CCCACCAAAGCGACGATCGGTAGCCGGACTGAGAGGTTGAACGGCCACATTGGGACTGAGA

CACGGCCCAGACTCCTACGGGAGGCAGCAGTGGGGGATATTGCACAATGGGCGAAAGCCTG

ATGCAGCGACGCCGCGTGAGGGAAGACGGTCTTCGGATTGTAAACCTCTGTCTTTGGGAA

GAAAATGACGGTACCCAAAGAGGAAGCTCCGGCTAACTACGTGCCAGCAGCCGCGGTAATA

CGTAGGGAGCAAGCGTTGTCCGGAATTACTGGGTGTAAAGGGAGCGTAGGCGGGATGGCAA

GTAGAATGTTAAATCCATCGGCTCAACCGGTGGCTGCGTTCTAAACTGCCGTTCTTGAGTG

AAGTAGAGGCAGGCGGAATTCCTAGTGTAGCGGTGAAATGCGTAGATATTAGGAGGAACAC

CAGTGGCGAAGGCGGCCTGCTGGGCTTTAACTGACGCTGAGGCTCGAAAGCGTGGGGAGCA

AACAGGATTAGATACCCTGGTAGTCCACGCCGTAAACGATGATTACTAGGTGTGGGGGAC

TGACCCCTTCCGTGCCGCAGTTAACACAATAAGTAATCCACCTGGGGAGTACGGCCGCAAG

GTTGAAACTCAAAGGAATTGACGGGGGCCCGCACAAGCAGTGGAGTATGTGGTTTAATTCG

AAGCAACGCGAAGAACCTTACCAGGTCTTGACATCGGATGCATAGCCTGGAGACAGGTGAA

GCCCTTCGGGGCATCCAGACAGGTGGTGCATGGTTGTCGTCAGCTCGTGTCGTGAGATGTT

GGGTTAAGTCCCGCAACGAGCGCAACCCTTATTATTAGTTGCTACGCAAGAGCACTCTAAT

GAGACTGCCGTTGACAAAACGGAGGAAGGTGGGGATGACGTCAAATCATCATGCCCCTTAT

GACCTGGGCTACACACGTACTACAATGGCACTTAAACAGAGGGCGGCGACACCGCGAGGTG

AAGCGAATCCCGAAAAAGTGTCTCAGTTCAGATTGCAGGCTGCAACCCGCCTGCATGAAGT

CGGAATTGCTAGTAATCGCGGATCAGCATGCCGCGGTGAATACGTTCCCGGGCCTTGTACA

CACCGCCCGTCACACCATGGGAGTCGGTAACACCCGAAGCCAGTAGCCTAACCGCAAGGGG

GGCGCTGTCGAAGGTGGGATTGATGACTGGGGTGAAGTCGTAACAAGGTAGCCGTATCGGA

AGGTGCGGCTGGATCACCTCCTTT

A. colihominis strain W2 16S rRNA (SEQ ID NO: 2)

CAAAGAGTTTGATCCTGGCTCAGGACGAACGCTGGCGGCGCGCCTAACACATGCAAGTCGA

ACGGGGCTTACATTTTGAAGTTTTCGGATGGACGAATGTAAGCTTAGTGGCGGACGGGTGA

GTAACACGTGAGCAACCTGCCTTTCAGAGGGGGATAACAGCCGGAAACGGCTGCTAATACC

GCATAATGTTGCGGGGCACATGCCCCTGCAACCAAAGGAGCAATCCGCTGAAAGATGGGC

TCGCGTCCGATTAGCCAGTTGGCGGGGTAACGGCCCACCAAAGCGACGATCGGTAGCCGGA

CTGAGAGGTTGAACGGCCACATTGGGACTGAGACACGGCCCAGACTCCTACGGGAGGCAGC

AGTGGGGGATATTGCACAATGGGCGAAAGCCTGATGCAGCGACGCCGCGTGAGGGAAGACG

-continued

GTCTTCGGATTGTAAACCTCTGTCTTTGGGGAAGAAAATGACGGTACCCAAAGAGGAAGCT
CCGGCTAACTACGTGCCAGCAGCCGCGGTAATACGTAGGGAGCAAGCGTTGTCCGGAATTA
CTGGGTGTAAAGGGAGCGTAGGCGGGATGGCAAGTAGAATGTTAAATCCATCGGCTCAACC
GGTGGCTGCGTTCTAAACTGCCGTTCTTGAGTGAAGTAGAGGCAGGCGGAATTCCTAGTGT
AGCGGTGAAATGCGTAGATATTAGGAGGAACACCAGTGGCGAAGGCGGCCTGCTGGGCTTT
AACTGACGCTGAGGCTCGAAAGCGTGGGGAGCAAACAGGATTAGATACCCTGGTAGTCCAC
GCCGTAAACGATGATTACTAGGTGTGGGGGACTGACCCCTTCCGTGCCGCAGTTAACACA
ATAAGTAATCCACCTGGGGAGTACGGCCGCAAGGTTGAAACTCAAAGGAATTGACGGGGGC
CCGCACAAGCAGTGGAGTATGTGGTTTAATTCGAAGCAACGCGAAGAACCTTACCAGGTCT
TGACATCGGATGCATAGCCTGGAGACAGGTGAAGCCCTTCGGGGCATCCAGACAGGTGGTG
CATGGTTGTCGTCAGCTCGTGTCGTGAGATGTTGGGTTAAGTCCCGCAACGAGCGCAACCC
TTATTATTAGTTGCTACGCAAGAGCACTCTAATGAGACTGCCGTTGACAAAACGGAGGAAG
GTGGGGATGACGTCAAATCATCATGCCCCTTATGACCTGGGCTACACACGTACTACAATGG
CACTTAAACAGAGGGCGGCGACACCGCGAGGTGAAGCGAATCCCGAAAAAGTGTCTCAGTT
CAGATTGCAGGCTGCAACCCGCCTGCATGAAGTCGGAATTGCTAGTAATCGCGGATCAGCA
TGCCGCGGTGAATACGTTCCCGGGCCTTGTACACACCGCCCGTCACACCATGGGAGTCGGT
AACACCCGAAGCCAGTAGCCTAACCGCAAGGGGGGCGCTGTCGAAGGTGGGATTGATGACT
GGGGTGAAGTCGTAACAAGGTAGCCGTATCGGAAGGTGCGGCTGGATCACCTCCTTT

*A. colihominis* strain W3 16S rRNA (SEQ ID NO: 3)

CAAAGGAGCAATCCGCTGAAAGATGGGCTCGCGTCCGATTAGCCAGTTGGCGGGGTAACGG
CCCACCAAAGCGACGATCGGTAGCCGGACTGAGAGGTTGAACGGCCACATTGGGACTGAGA
CACGGCCCAGACTCCTACGGGAGGCAGCAGTGGGGGATATTGCACAATGGGCGAAAGCCTG
ATGCAGCGACGCCGCGTGAGGGAAGACGGTCTTCGGATTGTAAACCTCTGTCTTTGGGGAA
GAAAATGACGGTACCCAAAGAGGAAGCTCCGGCTAACTACGTGCCAGCAGCCGCGGTAATA
CGTAGGGAGCAAGCGTTGTCCGGAATTACTGGGTGTAAAGGGAGCGTAGGCGGGATGGCAA
GTAGAATGTTAAATCCATCGGCTCAACCGGTGGCTGCGTTCTAAACTGCCGTTCTTGAGTG
AAGTAGAGGCAGGCGGAATTCCTAGTGTAGCGGTGAAATGCGTAGATATTAGGAGGAACAC
CAGTGGCGAAGGCGGCCTGCTGGGCTTTAACTGACGCTGAGGCTCGAAAGCGTGGGGAGCA
AACAGGATTAGATACCCTGGTAGTCCACGCCGTAAACGATGATTACTAGGTGTGGGGGAC
TGACCCCTTCCGTGCCGCAGTTAACACAATAAGTAATCCACCTGGGGAGTACGGCCGCAAG
GTTGAAACTCAAAGGAATTGACGGGGCCCGCACAAGCAGTGGAGTATGTGGTTTAATTCG
AAGCAACGCGAAGAACCTTACCAGGTCTTGACATCGGATGCATAGCCTGGAGACAGGTGAA
GCCCTTCGGGGCATCCAGACAGGTGGTGCATGGTTGTCGTCAGCTCGTGTCGTGAGATGTT
GGGTTAAGTCCCGCAACGAGCGCAACCCTTATTATTAGTTGCTACGCAAGAGCACTCTAAT
GAGACTGCCGTTGACAAAACGGAGGAAGGTGGGGATGACGTCAAATCATCATGCCCCTTAT
GACCTGGGCTACACACGTACTACAATGGCACTTAAACAGAGGGCGGCGACACCGCGAGGTG
AAGCGAATCCCGAAAAAGTGTCTCAGTTCAGATTGCAGGCTGCAACCCGCCTGCATGAAGT
CGGAATTGCTAGTAATCGCGGATCAGCATGCCGCGGTGAATACGTTCCCGGGCCTTGTACA

-continued

CACCGCCCGTCACACCATGGGAGTCGGTAACACCCGAAGCCAGTAGCCTAACCGCAAGGGG

GGCGCTGTCGAAGGTGGGATTGATGACTGGGGTGAAGTCGTAACAAGGTAGCCGTATCGGA

AGGTGCGGCTGGATCACCTCCTTT

*A. colihominis* strain W4 16S rRNA (SEQ ID NO: 4)
CAAAGAGTTTGATCCTGGCTCAGGACGAACGCTGGCGGCGCGCCTAACACATGCAAGTCGA

ACGGGGCTTACATTTTGAAGTTTTCGGATGGACGAATGTAAGCTTAGTGGCGGACGGGTGA

GTAACACGTGAGCAACCTGCCTTTCAGAGGGGATAACAGCCGGAAACGGCTGCTAATACC

GCATAATGTTGCGGGGGCACATGCCCCTGCAACCAAAGGAGCAATCCGCTGAAAGATGGGC

TCGCGTCCGATTAGCCAGTTGGCGGGGTAACGGCCCACCAAAGCGACGATCGGTAGCCGGA

CTGAGAGGTTGAACGGCCACATTGGGACTGAGACACGGCCCAGACTCCTACGGGAGGCAGC

AGTGGGGGATATTGCACAATGGGCGAAAGCCTGATGCAGCGACGCCGCGTGAGGGAAGACG

GTCTTCGGATTGTAAACCTCTGTCTTTGGGGAAGAAAATGACGGTACCCAAAGAGGAAGCT

CCGGCTAACTACGTGCCAGCAGCCGCGGTAATACGTAGGGAGCAAGCGTTGTCCGGAATTA

CTGGGTGTAAAGGGAGCGTAGGCGGGATGGCAAGTAGAATGTTAAATCCATCGGCTCAACC

GGTGGCTGCGTTCTAAACTGCCGTTCTTGAGTGAAGTAGAGGCAGGCGGAATTCCTAGTGT

AGCGGTGAAATGCGTAGATATTAGGAGGAACACCAGTGGCGAAGGCGGCCTGCTGGGCTTT

AACTGACGCTGAGGCTCGAAAGCGTGGGGAGCAAACAGGATTAGATACCCTGGTAGTCCAC

GCCGTAAACGATGATTACTAGGTGTGGGGGGACTGACCCCTTCCGTGCCGCAGTTAACACA

ATAAGTAATCCACCTGGGGAGTACGGCCGCAAGGTTGAAACTCAAAGGAATTGACGGGGGC

CCGCACAAGCAGTGGAGTATGTGGTTTAATTCGAAGCAACGCGAAGAACCTTACCAGGTCT

TGACATCGGATGCATAGCCTGGAGACAGGTGAAGCCCTTCGGGGCATCCAGACAGGTGGTG

CATGGTTGTCGTCAGCTCGTGTCGTGAGATGTTGGGTTAAGTCCCGCAACGAGCGCAACCC

TTATTATTAGTTGCTACGCAAGAGCACTCTAATGAGACTGCCGTTGACAAAACGGAGGAAG

GTGGGGATGACGTCAAATCATCATGCCCCTTATGACCTGGGCTACACACGTACTACAATGG

CACTAAAACAGAGGGCGGCGACACCGCGAGGTGAAGCGAATCCCGAAAAAGTGTCTCAGTT

CAGATTGCAGGCTGCAACCCGCCTGCATGAAGTCGGAATTGCTAGTAATCGCGGATCAGCA

TGCCGCGGTGAATACGTTCCCGGGCCTTGTACACACCGCCCGTCACACCATGGGAGTCGGT

AACACCCGAAGCCAGTAGCCTAACCGCAAGGGGGCGCTGTCGAAGGTGGGATTGATGACT

GGGGTGAAGTCGTAACAAGGTAGCCGTATCGGAAGGTGCGGCTGGATCACCTCCTTT

*Coprococcus* sp. strain M1 16S rRNA (SEQ ID NO: 5)
AACGAGAGTTTGATCCTGGCTCAGGATGAACGCTGGCGGCGTGCCTAACACATGCAAGTCG

AACGAAGCACTTACTTCCAAATCTTCGGAAGAGGAGGTACTTGACTGAGTGGCGGACGGGT

GAGTAACGCGTGGGGAACCTGCCCCGTACCGGGGGATAACAGTCAGAAATGACTGCTAATA

CCGCATAAGCGCACGAAGGCGCATGCTTTTGTGTGAAAAACTCCGGTGGTACGGGATGGTC

CCGCGTCTGATTAGCCAGTTGGCGGGGTAACGGCCCACCAAAGCGACGATCAGTAGCCGGC

CTGAGAGGGTGGACGGCCACATTGGGACTGAGACACGGCCCAGACTCCTACGGGAGGCAGC

AGTGGGGAATATTGCACAATGGGGGAAACCCTGATGCAGCGACGCCGCGTGAGCGAAGAAG

TATTTCGGTATGTAAAGCTCTGTCAGCAGGGAAGAAAATGACGGTACCTGACCAAGAAGCA

CCGGCTAAATACGTGCCAGCAGCCGCGGTAATACGTATGGTGCAAGCGTTATCCGGATTTA

CTGGGTGTAAAGGGAGCGTAGACGGAGGGGCAAGTCTGAAGTGAAAGCCCGGGGCCCAACC

CCGGGACTGCTTTGGAAACTGTCCGTCTGGAGTGCCGGAGAGGTAAGCGGAATTCCCAGTG

-continued

```
TAGCGGTGAAATGCGTAGATATTGGGAGGAACACCAGTGGCGAAGGCGGCTTACTGGACGG

TCACTGACGTTGAGGCTCGAAAGCGTGGGGAGCAAACAGGATTAGATACCCTGGTAGTCCA

CGCCGTAAACGATGACTACTAGGTGTCGGGTGGCAGAGCCATTCGGTGCCGCAGCCAACGC

AGTAAGTAGTCCACCTGGGGAGTACGTTCGCAAGAATGAAACTCAAAGGAATTGACGGGGA

CCCGCACAAGCGGTGGAGCATGTGGTTTAATTCGAAGCAACGCGAAGAACCTTACCTGGCC

TTGACATCCCCCTGACCGGCGCGTAATGGTGCCTTTCCTTCGGGACAGGGGAGACAGGTGG

TGCATGGTTGTCGTCAGCTCGTGTCGTGAGATGTTGGGTTAAGTCCCGCAACGAGCGCAAC

CCTTATCTTCAGTAGCCAGCACGCAGAGGTGGGCACTCTGGAGAGACTGCCAGGGACAACC

TGGAGGAAGGTGGGGATGACGTCAAATCATCATGCCCCTTATGGCCAGGGCTACACACGTG

CTACAATGGCGTAAACAGAGGGAAGCGAGCCCGCGAGGGGGAGCAAATCCCAAAAATAACG

TCCCAGTTCGGACTGCAGGCTGCAACCCGCCTGCACGAAGCTGGAATCGCTAGTAATCGCG

AATCAGCATGTCGCGGTGAATACGTTCCCGGGTCTTGTACACACCGCCCGTCACACCATGG

GAGTCGGTAACGCCCGAAGTCAGTGACCCAACCTCCGGGAGGGAGCTGCCGAAGGCGGGAC

CGGTAACTGGGGTGAAGTCGTAACAAGGTAGCCGTATCGGAAGGTGCGGCTGGATCACCTC

CTTT
```

*A. colihominis* strain M2 16S rRNA (SEQ ID NO: 6)

```
CAAAGAGTTTGATCCTGGCTCAGGACGAACGCTGGCGGCGCGCCTAACACATGCAAGTCGA

ACGGGGCTTACATTTTGAAGTTTTCGGATGGACGAATGTAAGCTTAGTGGCGGACGGGTGA

GTAACACGTGAGCAACCTGCCTTTCAGAGGGGATAACAGCCGGAAACGGCTGCTAATACC

GCATAATGTTGCGGGGGCACATGCCCCTGCAACCAAAGGAGCAATCCGCTGAAAGATGGGC

TCGCGTCCGATTAGCCAGTTGGCGGGGTAACGGCCCACCAAAGCGACGATCGGTAGCCGGA

CTGAGAGGTTGAACGGCCACATTGGGACTGAGACACGGCCCAGACTCCTACGGGAGGCAGC

AGTGGGGGATATTGCACAATGGGCGAAAGCCTGATGCAGCGACGCCGCGTGAGGGAAGACG

GTCTTCGGATTGTAAACCTCTGTCTTTGGGGAAGAAAATGACGGTACCCAAAGAGGAAGCT

CCGGCTAACTACGTGCCAGCAGCCGCGGTAATACGTAGGGAGCAAGCGTTGTCCGGAATTA

CTGGGTGTAAAGGGAGCGTAGGCGGGATGGCAAGTAGAATGTTAAATCCATCGGCTCAACC

GGTGGCTGCGTTCTAAACTGCCGTTCTTGAGTGAAGTAGAGGCAGGCGGAATTCCTAGTGT

AGCGGTGAAATGCGTAGATATTAGGAGGAACACCAGTGGCGAAGGCGGCCTGCTGGGCTTT

AACTGACGCTGAGGCTCGAAAGCGTGGGGAGCAAACAGGATTAGATACCCTGGTAGTCCAC

GCCGTAAACGATGATTACTAGGTGTGGGGGGACTGACCCCTTCCGTGCCGCAGTTAACACA

ATAAGTAATCCACCTGGGGAGTACGGCCGCAAGGTTGAAACTCAAAGGAATTGACGGGGC

CCGCACAAGCAGTGGAGTATGTGGTTTAATTCGAAGCAACGCGAAGAACCTTACCAGGTCT

TGACATCGGATGCATAGCCTGGAGACAGGTGAAGCCCTTCGGGGCATCCAGACAGGTGGTG

CATGGTTGTCGTCAGCTCGTGTCGTGAGATGTTGGGTTAAGTCCCGCAACGAGCGCAACCC

TTATTATTAGTTGCTACGCAAGAGCACTCTAATGAGACTGCCGTTGACAAAACGGAGGAAG

GTGGGGATGACGTCAAATCATCATGCCCCTTATGACCTGGGCTACACACGTACTACAATGG

CACTAAAACAGAGGGCGGCGACACCGCGAGGTGAAGCGAATCCCGAAAAAGTGTCTCAGTT

CAGATTGCAGGCTGCAACCCGCCTGCATGAAGTCGGAATTGCTAGTAATCGCGGATCAGCA

TGCCGCGGTGAATACGTTCCCGGGCCTTGTACACACCGCCCGTCACACCATGGGAGTCGGT

AACACCCGAAGCCAGTAGCCTAACCGCAAGGGGGCGCTGTCGAAGGTGGGATTGATGACT
```

-continued

GGGGTGAAGTCGTAACAAGGTAGCCGTATCGGAAGGTGCGGCTGGATCACCTCCTTT

*C. lactatifermentans* strain M3 16S rRNA (SEQ ID NO: 7)
CTTAGTGGCGGACGGGTGAGTAACGTGTGGGCAACCTGCCCTGTACTGGGGAATAATCATT

GGAAACGATGACTAATACCGCATGTGGTCCTCGGAAGGCATCTTCTGAGGAAGAAAGGATT

TATTCGGTACAGGATGGGCCCGCATCTGATTAGCTAGTTGGTGAGATAACAGCCCACCAAG

GCGACGATCAGTAGCCGACCTGAGAGGGTGATCGGCCACATTGGGACTGAGACACGGCCCA

AACTCCTACGGGAGGCAGCAGTGGGGAATATTGCACAATGGGCGAAAGCCTGATGCAGCAA

CGCCGCGTGAAGGATGAAGGGTTTCGGCTCGTAAACTTCTATCAATAGGGAAGAAAGAAAT

GACGGTACCTAAATAAGAAGCCCCGGCTAACTACGTGCCAGCAGCCGCGGTAATACGTAGG

GGGCAAGCGTTATCCGGAATTACTGGGTGTAAAGGGAGCGTAGGCGGCATGGTAAGCCAGA

TGTGAAAGCCTTGGGCTTAACCCGAGGATTGCATTTGGAACTATCAAGCTAGAGTACAGGA

GAGGAAAGCGGAATTCCTAGTGTAGCGGTGAAATGCGTAGATATTAGGAAGAACACCAGTG

GCGAAGGCGGCTTTCTGGACTGAAACTGACGCTGAGGCTCGAAAGCGTGGGGAGCAAACAG

GATTAGATACCCTGGTAGTCCACGCCGTAAACGATGAGTGCTAGGTGTCGGGGAGGAATCC

TCGGTGCCGCAGCTAACGCAATAAGCACTCCACCTGGGGAGTACGACCGCAAGGTTGAAAC

TCAAAGGAATTGACGGGGGCCCGCACAAGCGGTGGAGCATGTGGTTTAATTCGAAGCAACG

CGAAGAACCTTACCAAGGCTTGACATCCCGATGACCGCTCTAGAGATAGAGCTTCTCTTCG

GAGCATCGGTGACAGGTGGTGCATGGTTGTCGTCAGCTCGTGTCGTGAGATGTTGGGTTAA

GTCCCGCAACGAGCGCAACCCTTATCTTCAGTAGCCATCATTTAGTTGGGCACTCTGGAGA

GACTGCCGTGGATAACACGGAGGAAGGTGGGGATGACGTCAAATCATCATGCCCCTTATGT

CTTGGGCTACACACGTGCTACAATGGCTGGTAACAAAGTGACGCAAAACGGCGACGTTAAG

CAAATCACAAAAACCCAGTCCCAGTTCGGATTGTAGTCTGCAACTCGACTACATGAAGCTG

GAATCGCTAGTAATCGCGAATCAGCATGTCGCGGTGAATACGTTCCCGGGCCTTGTACACA

CCGCCCGTCACACCATGGGAGTTGGAAGCACCCGAAGTCGGTGACCTAACCGTAAGGAAGG

AGCCGCCGAAGGTGAAGCCAGTGACTGGGGTGAAGTCGTAACAAGGTAGCCGTATCGGAAG

GTGCGGCTGGATCACCTCCTTT

*P. capillosus* strain M4 16S rRNA (SEQ ID NO: 8)
TATTGAGAGTTTGATCCTGGCTCAGGATGAACGCTGGCGGCGTGCTTAACACATGCAAGTC

GAACGGAGAGCTAATGACAGAGGATTCGTCCAATGGATTTAGTTTCTTAGTGGCGGACGGG

TGAGTAACGCGTGAGGAACCTGCCTCGGAGTGGGGAATAACACAACGAAAGCTGTGCTAAT

ACCGCATGATGCAGCTGGGTCGCATGACTCTGGCTGCCAAAGATTTATCGCTCTGAGATGG

CCTCGCGTCTGATTAGCTGGTTGGCGGGGTAACGGCCCACCAAGGCGACGATCAGTAGCCG

GACTGAGAGGTTGGCCGGCCACATTGGGACTGAGACACGGCCCAGACTCCTACGGGAGGCA

GCAGTGGGGAATATTGGGCAATGGGCGCAAGCCTGACCCAGCAACGCCGCGTGAAGGAAGA

AGGCCCTCGGGTTGTAAACTTCTTTTGTCAGGGACGAAGCAAGTGACGGTACCTGACGAAT

AAGCCACGGCTAACTACGTGCCAGCAGCCGCGGTAATACGTAGGTGGCAAGCGTTATCCGG

ATTTACTGGGTGTAAAGGGCGTGTAGGCGGGATTGCAAGTCAGATGTGAAAACCACGGGCT

CAACCTGTGGCCTGCATTTGAAACTGCAGTTCTTGAGTACTGGAGAGGCAGACGGAATTCC

TAGTGTAGCGGTGAAATGCGTAGATATTAGGAGGAACACCAGTGGCGAAGGCGGTCTGCTG

GACAGCAACTGACGCTGAGGCGCGAAAGCGTGGGGAGCAAACAGGATTAGATACCCTGGTA

GTCCACGCTGTAAACGATGGATACTAGGTGTGGGGGGTCTGACCCCCTCCGTGCCGCAGTT

-continued

```
AACACAATAAGTATCCCACCTGGGGAGTACGATCGCAAGGTTGAAACTCAAAGGAATTGAC

GGGGGCCCGCACAAGCGGTGGAGTATGTGGTTTAATTCGAAGCAACGCGAAGAACCTTACC

AGGGCTTGACATCCCGATGACCGGACTAGAGATAGTCTTTTCTCTTCGGAGACATCGGTGA

CAGGTGGTGCATGGTTGTCGTCAGCTCGTGTCGTGAGATGTTGGGTTAAGTCCCGCAACGA

GCGCAACCCCTATTGTTAGTTGCTACGCAAGAGCACTCTAGCGAGACTGCCGTTGACAAAA

CGGAGGAAGGCGGGGACGACGTCAAATCATCATGCCCCTTATGTCCTGGGCCACACACGTA

CTACAATGGTGGTTAACAGAGGGAGGCAATACCGCGAGGTGGAGCAAACCCCTAAAAGCCA

TCCCAGTTCGGATTGCAGGCTGCAACCCGCCTGCATGAAGTTGGAATCGCTAGTAATCGCG

GATCAGCATGCCGCGGTGAATACGTTCCCGGGCCTTGTACACACCGCCCGTCACACCATGA

GAGTCGGGAACACCCGAAGTCCGTAGCCTAACCGCAAGGGGGCGCGGCCGAAGGTGGGTT

CGATAATTGGGGTGAAGTCGTAACAAGGTAGCCGTATCGGAAGGTGCGGCTGGATCACCTC

CTTT
```

*C. lactatifermentans* strain 2F1 16S rRNA
(SEQ ID NO: 9)

```
CTTAGTGGCGGACGGGTGAGTAACGTGTGGGCAACCTGCCCTGTACTGGGGAATAATCATT

GGAAACGATGACTAATACCGCATGTGGTCCTCGGAAGGCATCTTCTGAGGAAGAAAGGATT

TATTCGGTACAGGATGGGCCCGCATCTGATTAGCTAGTTGGTGAGATAACAGCCCACCAAG

GCGACGATCAGTAGCCGACCTGAGAGGGTGATCGGCCACATTGGGACTGAGACACGGCCCA

AACTCCTACGGGAGGCAGCAGTGGGGAATATTGCACAATGGGCGAAAGCCTGATGCAGCAA

CGCCGCGTGAAGGATGAAGGGTTTCGGCTCGTAAACTTCTATCAATAGGGAAGAAAGAAAT

GACGGTACCTAAATAAGAAGCCCCGGCTAACTACGTGCCAGCAGCCGCGGTAATACGTAGG

GGGCAAGCGTTATCCGGAATTACTGGGTGTAAAGGGAGCGTAGGCGGCATGGTAAGCCAGA

TGTGAAAGCCTTGGGCTTAACCCGAGGATTGCATTTGGAACTATCAAGCTAGAGTACAGGA

GAGGAAAGCGGAATTCCTAGTGTAGCGGTGAAATGCGTAGATATTAGGAAGAACACCAGTG

GCGAAGGCGGCTTTCTGGACTGAAACTGACGCTGAGGCTCGAAAGCGTGGGGAGCAAACAG

GATTAGATACCCTGGTAGTCCACGCCGTAAACGATGAGTGCTAGGTGTCGGGGAGGAATCC

TCGGTGCCGCAGCTAACGCAATAAGCACTCCACCTGGGGAGTACGACCGCAAGGTTGAAAC

TCAAAGGAATTGACGGGGGCCCGCACAAGCGGTGGAGCATGTGGTTTAATTCGAAGCAACG

CGAAGAACCTTACCAAGGCTTGACATCCCGATGACCGCTCTAGAGATAGAGCTTCTCTTCG

GAGCATCGGTGACAGGTGGTGCATGGTTGTCGTCAGCTCGTGTCGTGAGATGTTGGGTTAA

GTCCCGCAACGAGCGCAACCCTTATCTTCAGTAGCCATCATTTAGTTGGGCACTCTGGAGA

GACTGCCGTGGATAACACGGAGGAAGGTGGGGATGACGTCAAATCATCATGCCCCTTATGT

CTTGGGCTACACACGTGCTACAATGGCTGGTAACAAAGTGACGCAAAACGGCGACGTTAAG

CAAATCACAAAAACCCAGTCCCAGTTCGGATTGTAGTCTGCAACTCGACTACATGAAGCTG

GAATCGCTAGTAATCGCGAATCAGCATGTCGCGGTGAATACGTTCCCGGGCCTTGTACACA

CCGCCCGTCACACCATGGGAGTTGGAAGCACCCGAAGTCGGTGACCTAACCGTAAGGAAGG

AGCCGCCGAAGGTGAAGCCAGTGACTGGGGTGAAGTCGTAACAAGGTAGCCGTATCGGAAG

GTGCGGCTGGATCACCTCCTTT
```

*Lactobacillus salivarius* strain 2F2 16S rRNA
(SEQ ID NO: 10)

```
AATGAGAGTTTGATCCTGGCTCAGGACGAACGCTGGCGGCGTGCCTAATACATGCAAGTCG

AACGAAACTTTCTTACACCGAATGCTTGCATTCACCGTAAGAAGTTGAGTGGCGGACGGGT
```

```
GAGTAACACGTGGGTAACCTGCCTAAAAGAAGGGGATAACACTTGGAAACAGGTGCTAATA

CCGTATATCTCTAAGGATCGCATGATCCTTAGATGAAAGATGGTTCTGCTATCGCTTTTAG

ATGGACCCGCGGCGTATTAACTAGTTGGTGGGGTAACGGCCTACCAAGGTGATGATACGTA

GCCGAACTGAGAGGTTGATCGGCCACATTGGGACTGAGACACGGCCCAAACTCCTACGGGA

GGCAGCAGTAGGGAATCTTCCACAATGGACGCAAGTCTGATGGAGCAACGCCGCGTGAGTG

AAGAAGGTCTTCGGATCGTAAAACTCTGTTGTTAGAGAAGAACACGAGTGAGAGTAACTGT

TCATTCGATGACGGTATCTAACCAGCAAGTCACGGCTAACTACGTGCCAGCAGCCGCGGTA

ATACGTAGGTGGCAAGCGTTGTCCGGATTTATTGGGCGTAAAGGGAACGCAGGCGGTCTTT

TAAGTCTGATGTGAAAGCCTTCGGCTTAACCGGAGTAGTGCATTGGAAACTGGAAGACTTG

AGTGCAGAAGAGGAGAGTGGAACTCCATGTGTAGCGGTGAAATGCGTAGATATATGGAAGA

ACACCAGTGGCGAAAGCGGCTCTCTGGTCTGTAACTGACGCTGAGGTTCGAAAGCGTGGGT

AGCAAACAGGATTAGATACCCTGGTAGTCCACGCCGTAAACGATGAATGCTAGGTGTTGGA

GGGTTTCCGCCCTTCAGTGCCGCAGCTAACGCAATAAGCATTCCGCCTGGGGAGTACGACC

GCAAGGTTGAAACTCAAAGGAATTGACGGGGGCCCGCACAAGCGGTGGAGCATGTGGTTTA

ATTCGAAGCAACGCGAAGAACCTTACCAGGTCTTGACATCCTTTGACCACCTAAGAGATTA

GGTTTTCCCTTCGGGGACAAAGTGACAGGTGGTGCATGGCTGTCGTCAGCTCGTGTCGTGA

GATGTTGGGTTAAGTCCCGCAACGAGCGCAACCCTTGTTGTCAGTTGCCAGCATTAAGTTG

GGCACTCTGGCGAGACTGCCGGTGACAAACCGGAGGAAGGTGGGGACGACGTCAAGTCATC

ATGCCCCTTATGACCTGGGCTACACACGTGCTACAATGGACGGTACAACGAGTCGCAAGAC

CGCGAGGTTTAGCTAATCTCTTAAAGCCGTTCTCAGTTCGGATTGTAGGCTGCAACTCGCC

TACATGAAGTCGGAATCGCTAGTAATCGCGAATCAGCATGTCGCGGTGAATACGTTCCCGG

GCCTTGTACACACCGCCCGTCACACCATGAGAGTTTGTAACACCCAAAGCCGGTGGGGTAA

CCGCAAGGAGCCAGCCGTCTAAGGTGGGACAGATGATTGGGGTGAAGTCGTAACAAGGTAG

CCGTAGGAGAACCTGCGGCTGGATCACCTCCTTT
```

Lactobacillus reuteri strain 2F3 16S rRNA
(SEQ ID NO: 11)

```
GTGACGGTATCCAACCAGAAAGTCACGGCTAACTACGTGCCAGCAGCCGCGGTAATACGTA

GGTGGCAAGCGTTATCCGGATTTATTGGGCGTAAAGCGAGCGCAGGCGGTTGCTTAGGTCT

GATGTGAAAGCCTTCGGCTTAACCGAAGAAGTGCATCGGAAACCGGGCGACTTGAGTGCAG

AAGAGGACAGTGGAACTCCATGTGTAGCGGTGGAATGCGTAGATATATGGAAGAACACCAG

TGGCGAAGGCGGCTGTCTGGTCTGCAACTGACGCTGAGGCTCGAAAGCATGGGTAGCGAAC

AGGATTAGATACCCTGGTAGTCCATGCCGTAAACGATGAGTGCTAGGTGTTGGAGGGTTTC

CGCCCTTCAGTGCCGGAGCTAACGCATTAAGCACTCCGCCTGGGGAGTACGACCGCAAGGT

TGAAACTCAAAGGAATTGACGGGGGCCCGCACAAGCGGTGGAGCATGTGGTTTAATTCGAA

GCTACGCGAAGAACCTTACCAGGTCTTGACATCTTGCGCTAACCTTAGAGATAAGGCGTTC

CCTTCGGGGACGCAATGACAGGTGGTGCATGGTCGTCGTCAGCTCGTGTCGTGAGATGTTG

GGTTAAGTCCCGCAACGAGCGCAACCCTTGTTACTAGTTGCCAGCATTAAGTTGGGCACTC

TAGTGAGACTGCCGGTGACAAACCGGAGGAAGGTGGGGACGACGTCAGATCATCATGCCCC

TTATGACCTGGGCTACACACGTGCTACAATGGACGGTACAACGAGTCGCAAGCTCGCGAGA

GTAAGCTAATCTCTTAAAGCCGTTCTCAGTTCGGACTGTAGGCTGCAACTCGCCTACACGA

AGTCGGAATCGCTAGTAATCGCGGATCAGCATGCCGCGGTGAATACGTTCCCGGGCCTTGT
```

-continued
ACACACCGCCCGTCACACCATGGGAGTTTGTAACGCCCAAAGTCGGTGGCCTAACCTTTAT

GGAGGGAGCCGCCTAAGGCGGGACAGATGACTGGGGTGAAGTCGTAACAAGGTAGCCGTAG

GAGAACCTGCGGCTGGATCACCTCCTTT

---

We claim:

1. A method for preparing a feed additive composition comprising combining:
   a) a bacterial strain having a 16S ribosomal RNA sequence displaying at least 97.0% sequence similarity to a 16S ribosomal RNA sequence of an *Anaerotruncus colihominis* strain W1 deposited at Westerdijk Fungal Biodiversity Institute (WFDB) under number CBS 146120;
   b) a bacterial strain having a 16S ribosomal RNA sequence displaying at least 97.0% sequence similarity to a 16S ribosomal RNA sequence of an *Anaerotruncus colihominis* strain W2 deposited at WFDB under number CBS 146122;
   c) a bacterial strain having a 16S ribosomal RNA sequence displaying at least 97.0% sequence similarity to a 16S ribosomal RNA sequence of an *Anaerotruncus colihominis* strain W3 deposited at WFDB under number CBS 146123; and
   d) a bacterial strain having a 16S ribosomal RNA sequence displaying at least 97.0% sequence similarity to a 16S ribosomal RNA sequence of an *Anaerotruncus colihominis* strain W4 deposited at WFDB under number CBS 146121.

2. The method of claim 1, wherein a) the *A. colihominis* strain W1 is an *A. colihominis* strain W1 (CBS 146120); b) the *A. colihominis* strain W2 is an *A. colihominis* strain W2 (CBS 146122); c) the *A. colihominis* strain W3 is an *A. colihominis* strain W3 (CBS 146123); and d) the *A. colihominis* strain W4 is an *A. colihominis* strain W4 (CBS 146121) either (i) alone; or (ii) in combination with a culture supernatant derived from each of these strains.

3. The method of claim 1, further comprising combining one or more enzymes with the feed additive composition.

4. The method of claim 3, wherein the one or more enzymes are selected from the group consisting of a phytase, a protease, an amylase, a xylanase and a beta-glucanase.

5. The method of claim 1, wherein at least about $1 \times 10^3$ CFU/g feed additive composition to at least about $1 \times 10^9$ CFU/g feed additive composition is combined to form the feed additive composition.

6. The method of claim 1, further comprising packaging the feed additive composition.

\* \* \* \* \*